(12) United States Patent
Changsrivong et al.

(10) Patent No.: US 9,482,255 B2
(45) Date of Patent: Nov. 1, 2016

(54) MULTI-LATCHING MECHANISMS AND RELATED METHODS

(71) Applicant: BAL SEAL ENGINEERING, INC., Foothill Ranch, CA (US)

(72) Inventors: Derek Changsrivong, Foothill Ranch, CA (US); Rob Sjostedt, Foothill Ranch, CA (US); Hugh Cook, Foothill Ranch, CA (US); Rick Dawson, Foothill Ranch, CA (US)

(73) Assignee: Bal Seal Engineering, Inc., Foothill, CA (US)

( * ) Notice: Subject to any disclaimer, the term of this patent is extended or adjusted under 35 U.S.C. 154(b) by 857 days.

(21) Appl. No.: 13/693,289

(22) Filed: Dec. 4, 2012

(65) Prior Publication Data

US 2013/0149029 A1   Jun. 13, 2013

Related U.S. Application Data

(60) Provisional application No. 61/568,529, filed on Dec. 8, 2011.

(51) Int. Cl.
*F16B 17/00* (2006.01)
*A61N 1/375* (2006.01)
*F16B 21/18* (2006.01)
*H01R 13/187* (2006.01)
(Continued)

(52) U.S. Cl.
CPC .............. *F16B 17/00* (2013.01); *A61N 1/3752* (2013.01); *F16B 21/186* (2013.01); *H01R 13/187* (2013.01); *H01R 24/58* (2013.01); *F16B 2001/0035* (2013.01); *Y10T 29/49947* (2015.01); *Y10T 403/7039* (2015.01)

(58) Field of Classification Search
None
See application file for complete search history.

(56) References Cited

U.S. PATENT DOCUMENTS 3,174,500 A *  3/1965  Johnson ................. C01G 43/06
                                                137/116.3
4,678,210 A   7/1987  Balsells
(Continued)

FOREIGN PATENT DOCUMENTS

DE     198 07 663 A1   9/1999
EP     0 326 096 A2    8/1989
(Continued)

OTHER PUBLICATIONS

English translation of Office action dated Jan. 6, 2015 from corresponding Chinese Application No. 201210526646.4 (11 pages).
(Continued)

*Primary Examiner* — Victor MacArthur
(74) *Attorney, Agent, or Firm* — Klein, O'Neill & Singh, LLP

(57) ABSTRACT

Dual directional latch devices or connectors are described wherein a first connector component and a second connector component have a first latched position and a second latched position when moving in a first direction and wherein movement in a second direction is also possible when a restriction feature is overcome. As described, opposing magnetic forces, pneumatic pressure, spring force, and a crushable force may be incorporated so that further movement in the second direction must overcome the restriction feature. The dual direction latch devices may be used with articles of manufacture such as with implantable medical devices, door panels, airplane panels, and drilling devices to name a few.

15 Claims, 18 Drawing Sheets

(51) Int. Cl.
*H01R 24/58* (2011.01)
*F16B 1/00* (2006.01)

(56) References Cited

U.S. PATENT DOCUMENTS

| | | | |
|---|---|---|---|
| 4,804,290 A * | 2/1989 | Balsells | F04B 53/143 |
| | | | 277/437 |
| 4,872,710 A | 10/1989 | Konecny et al. | |
| 5,413,595 A * | 5/1995 | Stutz, Jr. | A61N 1/3752 |
| | | | 607/37 |
| 5,791,930 A | 8/1998 | Tabata et al. | |
| 6,638,098 B2 | 10/2003 | Yamaoka | |
| 6,672,565 B2 * | 1/2004 | Russell | E21B 21/106 |
| | | | 251/297 |
| 6,725,096 B2 | 4/2004 | Chinn | |
| 6,913,480 B2 | 7/2005 | Wilcox | |
| 7,914,315 B2 | 3/2011 | Kuhn | |
| 8,052,459 B2 | 11/2011 | Smith et al. | |
| 2002/0122690 A1 | 9/2002 | Poon et al. | |
| 2003/0096526 A1 | 5/2003 | Balsells | |
| 2004/0005802 A1 | 1/2004 | Lamirey | |
| 2008/0254670 A1 | 10/2008 | Balsells et al. | |
| 2008/0255631 A1 * | 10/2008 | Sjostedt | A61N 1/3752 |
| | | | 607/37 |
| 2009/0149053 A1 * | 6/2009 | Chansrivong | H01R 13/15 |
| | | | 439/349 |
| 2010/0029145 A1 * | 2/2010 | Balsells | H01R 13/03 |
| | | | 439/827 |
| 2010/0199493 A1 * | 8/2010 | Chansrivong | H01R 13/15 |
| | | | 29/869 |
| 2010/0311266 A1 * | 12/2010 | Dilmaghanian | A61N 1/3752 |
| | | | 439/345 |
| 2011/0014005 A1 | 1/2011 | Shinozaki | |

FOREIGN PATENT DOCUMENTS

| | | |
|---|---|---|
| EP | 2 259 383 A1 | 12/2010 |
| FR | 2 390 618 A1 | 12/1978 |
| GB | 2 194 298 A | 3/1988 |
| WO | WO 03/067713 A1 | 8/2003 |
| WO | WO 2009/126968 A1 | 10/2009 |

OTHER PUBLICATIONS

Extended European Search Report dated May 15, 2013 from corresponding European Application No. 12195900.1 (9 pages).
Extended European Search Report from related European Patent Application No. 10005812.2 (6 pages).

* cited by examiner

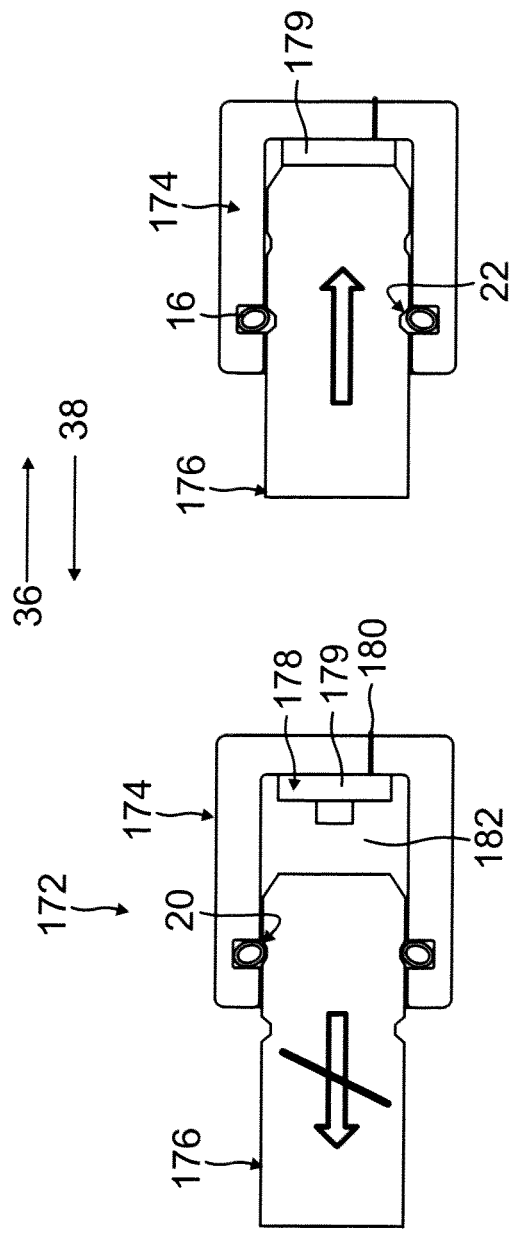

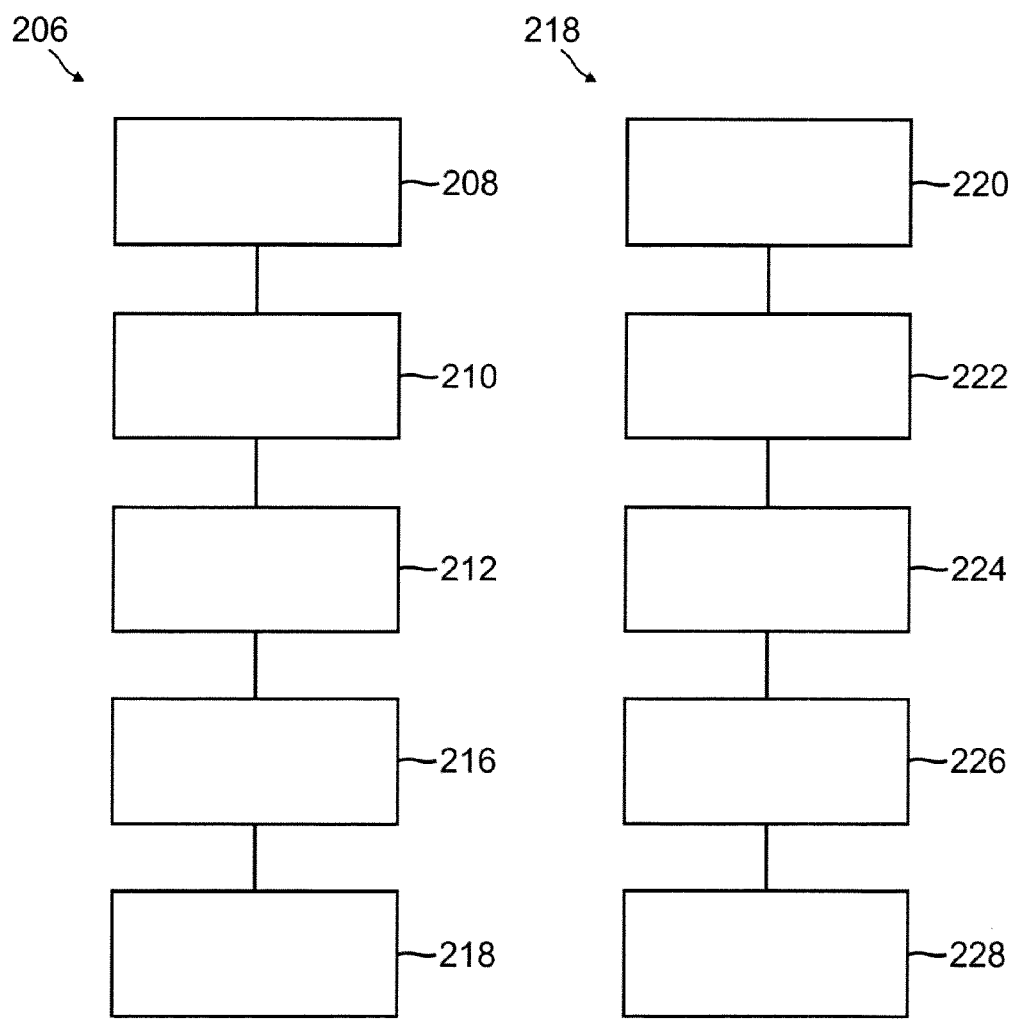

MULTI-LATCHING MECHANISMS AND RELATED METHODS

CROSS-REFERENCE TO RELATED APPLICATION

This is a regular utility application of provisional application No. 61/568,529, filed Dec. 8, 2011, the contents of which are expressly incorporated herein by reference. This application may be related to and expressly incorporates by reference application Ser. No. 13/239,153, filed Sep. 21, 2011, the contents of which are expressly incorporated herein by reference.

FIELD OF ART

Latching and locking devices and assemblies and related methods are generally discussed herein with specific discussions extended to latching devices that latch when inserted in a first direction and locks when withdraws in a second direction but that when further inserted in the first direction, permits latching in the second direction. The devices, assemblies and methods are capable of dual-directional latching. Further aspects of the present devices, assemblies and methods include restriction features, such as opposing forces, alignment slots, shear pins, wave springs, rupture blocks, etc., for limiting further insertion in the first direction until the restriction features are overcome, which then permits latching in the second direction.

BACKGROUND

Conventional connection mechanisms utilize a canted coil spring and specific groove geometries between a first connector component and a second connector component, such as a housing and a pin, to achieve locking or latching, see, for example, U.S. Pat. Nos. 4,678,210 and 5,082,390. In the case of a locking device, the device becomes permanently locked, which means the device cannot reverse direction without permanently damaging the canted coil spring. In the case of a latching device, the device can be unlatched, i.e., reverse direction, without damaging the spring. Thus, latching is understood to include a locking type or an unlatching or unlatch-able type. This is permitted by incorporating a groove geometry that allows the minor axis of the spring to compress so that it no longer obstructs relative movement between the first connector component and the second connector component.

Locking is achieved between two mating parts (e.g., cylindrical part or shaft and a housing) where a tapered bottom groove exists in the housing and holds an axial spring and where the tapered bottom groove aligns with a corresponding groove on the cylindrical part which accepts the spring. The tapered bottom groove is configured, such as being sized and shaped. In such a way that the spring compresses along the minor axis upon insertion to permit installation but not upon removal when moving in the reverse direction, such as by angling or rotating the spring after being latched so that unlatching requires compressing the spring along the major axis, which is not possible without destroying the spring. Because the spring does not compress along the major axis upon removal, due to its position within the groove, it does not unlatch and remain locked. The spring is forced to compress along the major axis when attempting to remove the cylindrical part, which does not materially or significantly compress, to ensure locking. As such, removal of a "locked" device causes permanent damage to the spring if forced to disassemble. Again, this is due to the characteristic of a canted coil spring only being allowed a minimal compression along the major axis.

SUMMARY

The present device, system, and method make it possible for a locking connection to be disconnected when moving in the opposite direction from the insertion or installation direction, which previously was not possible without damaging the spring, as discussed above. In one example, the device, system, and method include incorporating or providing a sufficiently deep secondary groove in addition to a primary groove to allow the canted coil spring to move to the secondary groove and then rotate back to its relaxed vertical position. Unlike when in the primary groove, the spring is not held when in the secondary groove against rotation and has room to rotate in the opposite direction that it experienced during insertion. The leading edge of the secondary groove makes contact with the canted coil spring and rotates it, thus allowing for removal of the canted coil spring from the secondary groove and back into the first groove, but being rotated for removal or unlocking. Here the canted coil spring is orientated so that the cylindrical part can be completely unlatched.

In an example, a restriction feature is incorporated in the connector assembly for making moving the spring into the secondary groove more difficult but not impossible. This added restriction feature may be desired to ensure purposeful locking so that unlocking may only occur when a positive step is taken to overcome the restriction feature to then permit further movement of the spring into the secondary groove, which enables spring rotation for subsequent unlocking or unlatching. In another example, the restriction feature is an alarm or warning.

Thus, once the cylindrical part is inserted into the housing and engages the primary groove, the canted coil spring experiences a removal lock, i.e., it cannot be removed by moving the cylindrical part in the reverse direction without damaging the spring, also referred to as a single step lock. To unlock the assembly, essentially by converting a locking device into a latching device that permits unlocking or unlatching, the spring is rotated to permit reversal of the cylindrical part. In an example, the cylindrical part is further inserted into the housing, or the housing is move relative to the cylindrical part, in the same direction as the original direction for locking to permit spring rotation. During the further insertion step, the spring engages a secondary groove, which is larger than the primary groove. By larger, it is understood to mean wider, deeper, or both wider and deeper than the primary groove. Because the secondary groove is larger, the spring is not so constrained and permitted to rotate. Preferably, the secondary groove does not restrain the spring. From this point within the secondary groove, the device can be unlatched by moving the cylindrical part in the removal direction. Thus, the device is capable of dual directional latching. An aspect of the present device, system, and assembly includes a restriction feature that requires an affirmative step before moving in the second direction is permitted.

The combination primary and secondary grooves may optionally be incorporated in the housing or in the cylindrical part. In other words, the housing can have a single groove or two grooves and the pin can have the corresponding two grooves or single groove.

In addition to allowing dual directional latching, the larger secondary groove following the primary groove can provide a lower removal force as compared to removal from the primary groove in latching applications. In other words, the force to move the spring from the secondary groove to separate the pin from the housing is lower than the force to move the spring when it is in the first groove and moving it in the same insertion direction.

Thus, once the cylindrical part is inserted into the housing and engages the primary groove, the canted coil spring experiences a removal lock. To unlatch, the cylindrical part is first inserted further into the housing. In one example, when the pin is further inserted, a secondary groove located on the pin moves into the housing so that the spring engages the secondary groove. In a specific example, the secondary groove is larger than the first groove. Once in the larger secondary groove, the spring is able to rotate and be unlatched by moving the cylindrical part in the removal direction, opposite the insertion direction. By larger, the groove can have a larger groove depth, a larger volumetric space, or both.

The connectors described herein may be use with articles of manufacture to secure the articles together but permit separation upon performing a spring rotation step to permit unlatching and separation of the pin from the housing.

A still further feature of the present device, system, and method is understood to include a connector comprising a first connector component mated with a second connector component. A groove is provided in or on the first connector component or the second connector component and a pair of grooves located in or on the other one of the first connector component or the second connector component. The groove has two sidewalls and a bottom wall and the pair of grooves comprises a first groove having a first depth and a second groove having a second depth, which differs from the first depth. A canted coil spring positioned in the first groove and the groove and is movable to be seated in the second groove and the groove and wherein a restriction feature prevents the first connector component from moving relative to the second connector component until overcome by an insertion force to restrict the canted coil spring from being engaged by the second groove and the groove.

In an embodiment, the first connector component is a pin or a housing and the second connector component is the other one of the pin or the housing.

In another embodiment, the second connector component s attached to an article of manufacture.

In yet another embodiment, an implantable medical device is provided and wherein the first connector component is located in a header of the implantable medical device.

In yet another embodiment, the restriction feature is a helical spring, opposing forces, a wave spring, or air pressure.

In yet another embodiment, the restriction feature is an open switch.

In yet another embodiment, the restriction feature is a collapsible or deflectable component located inside a bore.

In yet another embodiment, an article of manufacture is attached to the first connector component or the second connector component.

Aspects of the present disclosure further include a method of manufacturing a connector comprising forming a first connector component having a groove and forming a second connector component having a primary groove and a secondary groove. The method further includes sizing a first common groove between the groove and the primary groove with a first spring holding space and a second common groove between the groove and the secondary groove with a second spring holding space, which is larger than the first common groove. The method further includes the step of forming a restriction feature to limit relative movement between the first connector component and the second connector component until overcome by an insertion force. Wherein the first common groove is sized and configured to receive a canted coil spring and loading the canted coil spring along its major axis and wherein the second common groove is sized and configured to receive the canted coil spring and not load the spring along its major axis.

In an embodiment, the method further includes the step of attaching an article of manufacture to the first connector component or the second connector component.

In an embodiment, the method further includes the step of placing the first connector component in a header of an implantable medical device.

In yet another embodiment, the method further includes the step of providing a plurality of spaced apart primary grooves.

In an example, the restriction feature is a sub-connector assembly comprising a pin having an external groove located inside an outer bore and latched to an inner bore comprising an inner groove and a canted coil spring.

In a further aspect of the present disclosure, a connector is provided comprising a housing comprising a bore and a housing groove having a housing groove configuration. The connector further including a pin comprising a pin groove having a pin groove configuration; a second groove located adjacent the housing groove or the pin groove, the second groove having a second groove configuration with a second groove depth that differs from the housing groove configuration and the pin groove configuration. The connector further comprising an axial canted coil spring disposed in the bore in a first spring position in a first common groove defined by a combination of the housing groove and the pin groove and is movable relative to the pin and the housing to a second common groove defined by a combination of the housing groove and the second groove or a combination of the pin groove and the second groove. Wherein a restriction feature is provided to restrict relative movement between the housing and the pin to restrict the axial canted coil spring from moving to the second common groove until overcome by an insertion force.

BRIEF DESCRIPTION OF THE DRAWINGS

The various embodiments of the present connectors, systems, and associated methods now will be discussed in detail with an emphasis on highlighting the advantageous features. These embodiments depict the novel and non-obvious connectors shown in the accompanying drawings, which are for illustrative purposes only. These drawings include the following figures, in which like numerals indicate like parts:

FIG. 8A shows a schematic cross-sectional side view of an alternative dual direction connector, which shows a second connector component located in a bore of a first connector component and a restriction feature that embodying an electrical switch or trigger.

FIG. 8B shows a schematic cross-sectional side view of the dual direction connector of FIG. 8A with the restriction feature energized and the second connector component further into the bore of the first connector component so that the spring is latched in a second latched position.

FIG. 11 is a process flow diagram depicting a method of use of a connector assembly.

FIG. 12 is a process flow diagram depicting a method of manufacturing a connector assembly.

DETAILED DESCRIPTION

The embodiments of the present connectors, systems, and associated methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unit or a unitary piece and whereas a unitary piece means a singularly formed single piece, such as a singularly formed mold or cast. Still further, the terms "first" and "second" used herein are understood as identifiers only to distinguish between similar but different components but not structurally limiting. Thus, unless the context indicates otherwise. "first" and "second" are not limiting terms.

Figure 1A:
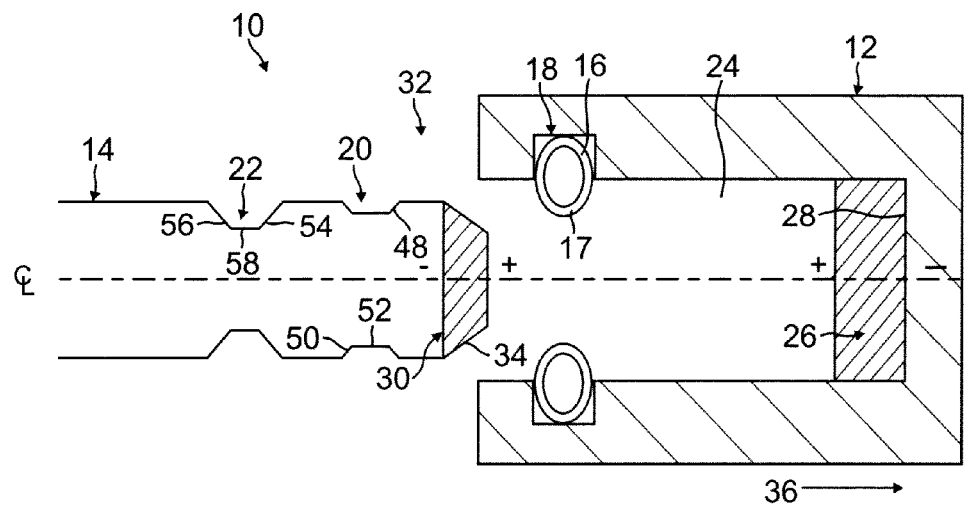
FIG. 1A shows a schematic cross-sectional side view of a dual direction connector, which shows a second connector component aligned for insertion into a bore of a first connector component and a restriction feature provided to restrict further advancement.

FIG. 1A shows a partial cross-sectional side view of a connector assembly provided in accordance with aspects of the present device, system, and method, which is generally designated 10. The connector assembly, or simply connector, comprises a first connector component 12, a second connector component 14, and a canted coil spring 16. The connector is generally symmetrical about a centerline CL of the second connector component 14 and/or of the first connector component 12. In one exemplary embodiment, the first connector component 12 is a housing comprising a housing groove 18 and the second connector component 14 is a cylindrical member or pin 14 comprising a primary pin groove 20 and a secondary pin groove 22, which is larger than the primary pin groove. By larger, it is understood to mean larger in width, in depth, or both width and depth. In another embodiment, the first and second connector components are reversed.

With continued reference to FIG. 1A, the first connector component 12 has a bore 24 sized to receive the second connector component 14 and is sufficiently deep to so that the second connector component 14 can engage the spring 16 at the secondary groove 22, as further discussed below. The bore 24 and the second connector component 14 may be round about the centerline CL with other shapes contemplated, such as square, rectangular, oval, etc. A magnet 26 having north and south poles, designated with positive "+" and negative "−" signs, is mounted inside the bore 24. In one example, the magnet 26 is placed in contact with the end wall 28 of the first connector component 12, such as by using a fastener, detents, screws, adhesive, or other mechanical means. Magnets useable herein can include permanent, temporary, and electromagnetic types. For example, the magnet 26 can be a rare earth magnet, such as a neodymium magnet or a samarium-cobalt magnet or can be controlled or energized as desired, such as through powering on or off electrically charged particles that produce electromagnetic forces.

Like the first connector component 12, the second connector component 14 incorporates a magnet 30. In a specific embodiment, the magnet 30 is incorporated at the distal end or tip 32 but can be placed elsewhere depending on the particular application. The magnet 30 can incorporate a nose section with a taper 34 to facilitate insertion of the second connector component 14 in the first direction 36 into the bore 24 of the first connector component 12. Looking at the upper spring 16 sectional view, the taper 34 causes the coil 17 to rotate counterclockwise as the second connector component 14 is inserted into the bore 24. The magnet 30 can be of the same type as the magnet 26 incorporated in the first connector component 12 or be dissimilar. The magnet 30 may be mounted on the second connector component 14 using a fastener or adhesive and is mounted so that its north and south poles oppose the north and south poles on the magnet 26 of the first connector component 12 for reasons further discussed below.

Figure 1B:
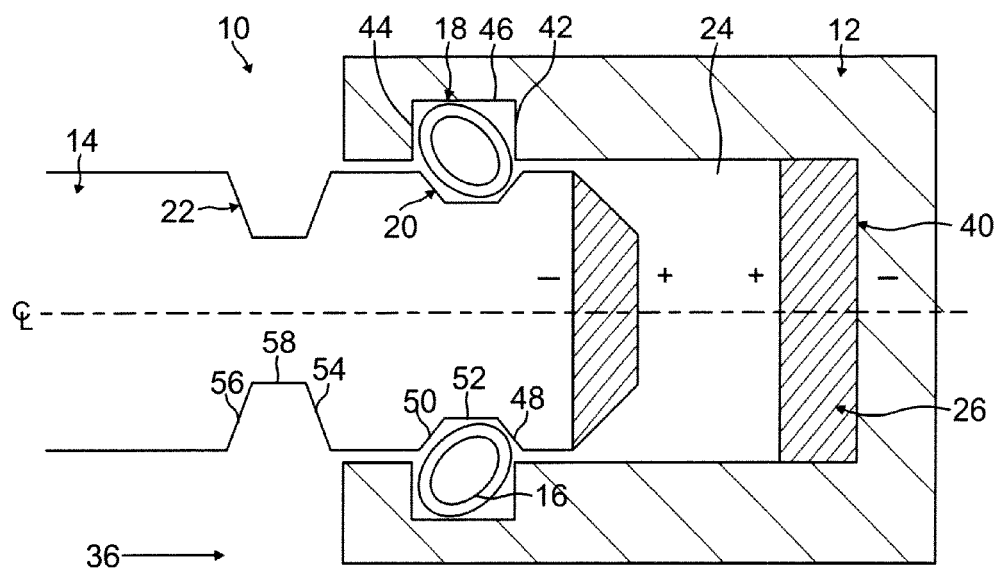
FIG. 1B shows a schematic cross-sectional side view of the dual direction connector of FIG. 1A with the first connector component latched in a first position with the second connector component.

With reference now to FIG. 1B, the first connector component 12 and the second connector component 14 are shown locked together in a first latched position. The connector 10 is latched in the first position by moving the cylindrical member or second connector component 14 in the first direction 36 so that the spring 16 is oriented as shown between the housing groove 18 and the primary groove 20 and is prevented, i.e., locked, from moving in the second direction 38 due to the orientation of the major axis. i.e., the longer axis of each spring coil, of the spring 16. As oriented in FIG. 1B, the spring 16 would necessarily compress along its major axis. i.e., the longer axis of each spring coil, to permit removal in the second direction 38. The other axis being the shorter or minor axis. However, it is generally not possible to compress the spring along its major axis to provide sufficient clearance for removable of the second connector component 14 without destroying the spring. During insertion of the second connector component 14, the insertion force progressively increases as the opposing magnetic forces of the two magnets 26, 30 come closer and closer together. Although the opposing magnetic forces tend to push the second connector component 14 and the first connector component 12 away from one another when in the first latched position, the spring 16 prevents the second connector component 14 from moving in the second direction 38. At the same time, further insertion of the second connector component 14 into the bore 24 of the first connector component 12 to move the connector into a second latched position (FIG. 1C) is restricted by the opposing magnetic forces. The restriction is not absolute and can be overcome by an insertion force that is greater than the opposing forces of the two magnets. The opposing forces can also be regulated by selecting magnets that provide the desired opposing force values. Thus, the magnets 26, 30 are understood to be a restriction feature 40 that restricts movement of the connector 10 from the first latched position to the second latched position.

In one example, the housing groove 18 comprises two side walls 42, 44 and a bottom wall 46 located therebetween that is generally flat, i.e., generally orthogonal, to one or both side walls. However, the bottom wall 46 may be tapered, such as a V-groove, or has a complex geometry relative to one or both side walls 42, 44.

Like the housing groove 18, the primary pin groove 20 and the secondary pin groove 22 both have side walls 48, 50, 54, 56 and a bottom wall 52, 58. In one exemplary embodiment, the primary pin groove 20 comprises two tapered side walls 48, 50 that taper outwardly in the direction away from the centerline and a flat bottom wall 52. In another example, the primary groove 20 is a V-groove formed by the two side walls without a bottom wall. In another example, the side walls 48, 50 may be straight and the bottom wall 52 may be tapered without deviating from the spirit and scope of the present assembly and method. In another example, the bottom wall 52 is complex, i.e., having multiple surfaces with varying angles. The secondary groove 22 may have a similar groove configuration as the primary groove 20 with one exception, it is larger than the primary groove. By larger, the groove width, the groove depth, or both the depth and the width of the secondary groove are larger than that of the primary groove. As further discussed below, the larger secondary groove provides sufficient room or space for the spring to rotate to enable unlocking or unlatching.

Figure 1C:
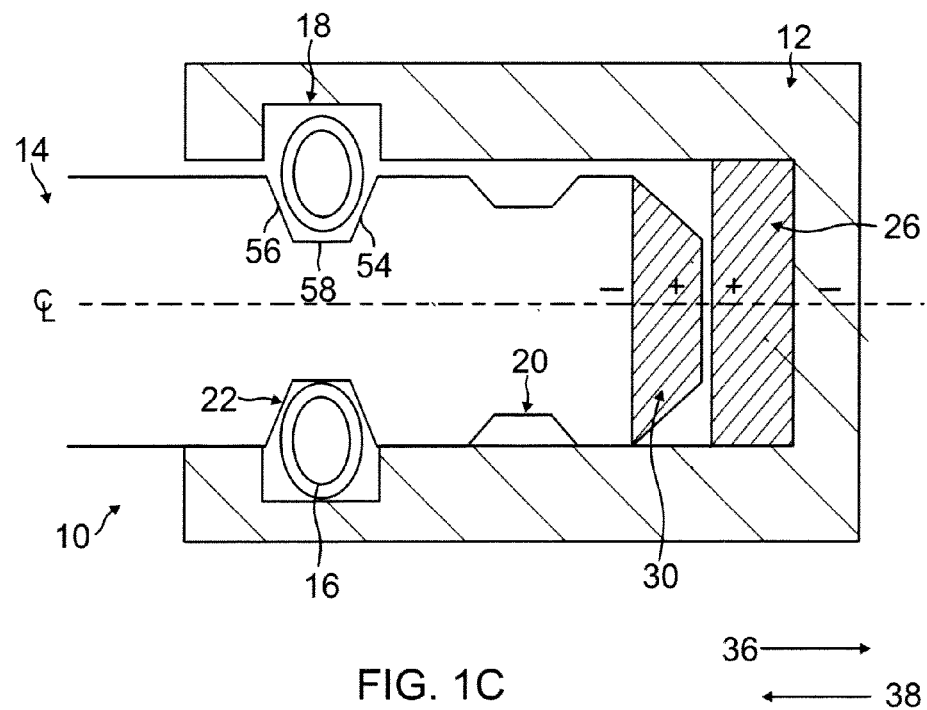
FIG. 1C shows a schematic cross-sectional side view of the dual direction connector of FIG. 1A with the first connector component latched in a second position with the second connector component and the opposing forces of the restriction feature overcome by an insertion force.

Refer now to FIG. 1C, a schematic cross-sectional side view of the connector assembly 10 of FIG. 1A is shown with the second connector component 14 further inserted into the first connector component 12 so that the spring 16 is now captured between the housing groove 18 and the secondary groove 22. The connector 10 is moved to the second position as shown in FIG. 1C, from the first position shown in FIG. 1B, by first applying a force to unlatch the spring 16 from the first position and overcoming the restriction feature 40, which in the present embodiment is the opposing forces of the magnets 26, 30, to move in the first direction 36. The moving force to move the connector to the second position progressively increases as the opposing north poles are forced to come closer than when the connector is in the first latched position. In the relaxed second position. FIG. 1C, the spring 16 and more particularly the major axis of the coils is permitted to rotate generally more vertically because of the larger secondary groove 22 compared to the relatively smaller primary groove 20. Once allowed to rotate to its relaxed position, the spring 16 can now be counter-rotated by moving the pin in the second direction 38 relative to the first connector component 12 to unlock or unlatch the pin from the housing. In particular, the tapered side wall 54 of the secondary groove 22 pushes against the spring 16 to compress it along the minor axis. i.e., shorter axis of the coils, during retraction of the pin in the second direction 26. The retraction is further facilitated by the opposing forces of the magnets 26, 30, which reduce the force needed to remove the second connector component 14 from the first connector component compared to a similar connector without any magnets. As shown, the spring 16 is an axial canted coil spring. However, a radial canted coil spring is contemplated. In contrast, the tapered side wall 48 of the primary groove 20 generally loads the spring along its major axis in FIG. 1B and therefore does not permit retraction in the second direction 26.

Figure 1D:
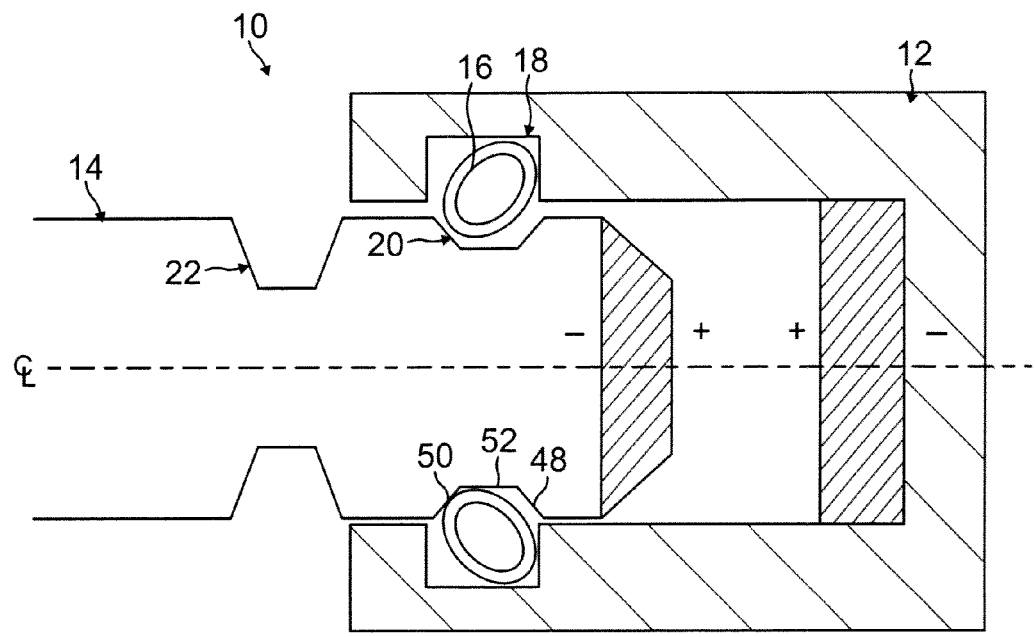
FIG. 1D shows a schematic cross-sectional side view of the dual direction connector of FIG. 1A with the first connector component returning to the first latched position with the second connector component but with the spring angle rotated for removal.

FIG. 1D shows the connector 10 returning to its first latched position after moving to its second latched position. As shown, the spring 16 is captured by the first connector groove 18 and the primary groove 20 but with the major axis of the coils of the spring 16 rotated in a different angle than when being captured the first time by the primary groove (FIG. 1B). The second connector component 14 may be completely separated from the first connector component 12 by further moving in the second direction 38. Note that during the retraction process to remove the second connector component from the first connector component, sidewall 48 of the primary groove 20 is now configured to compress the spring along its minor axis as the spring's major axis has now rotated.

Figure 1E:
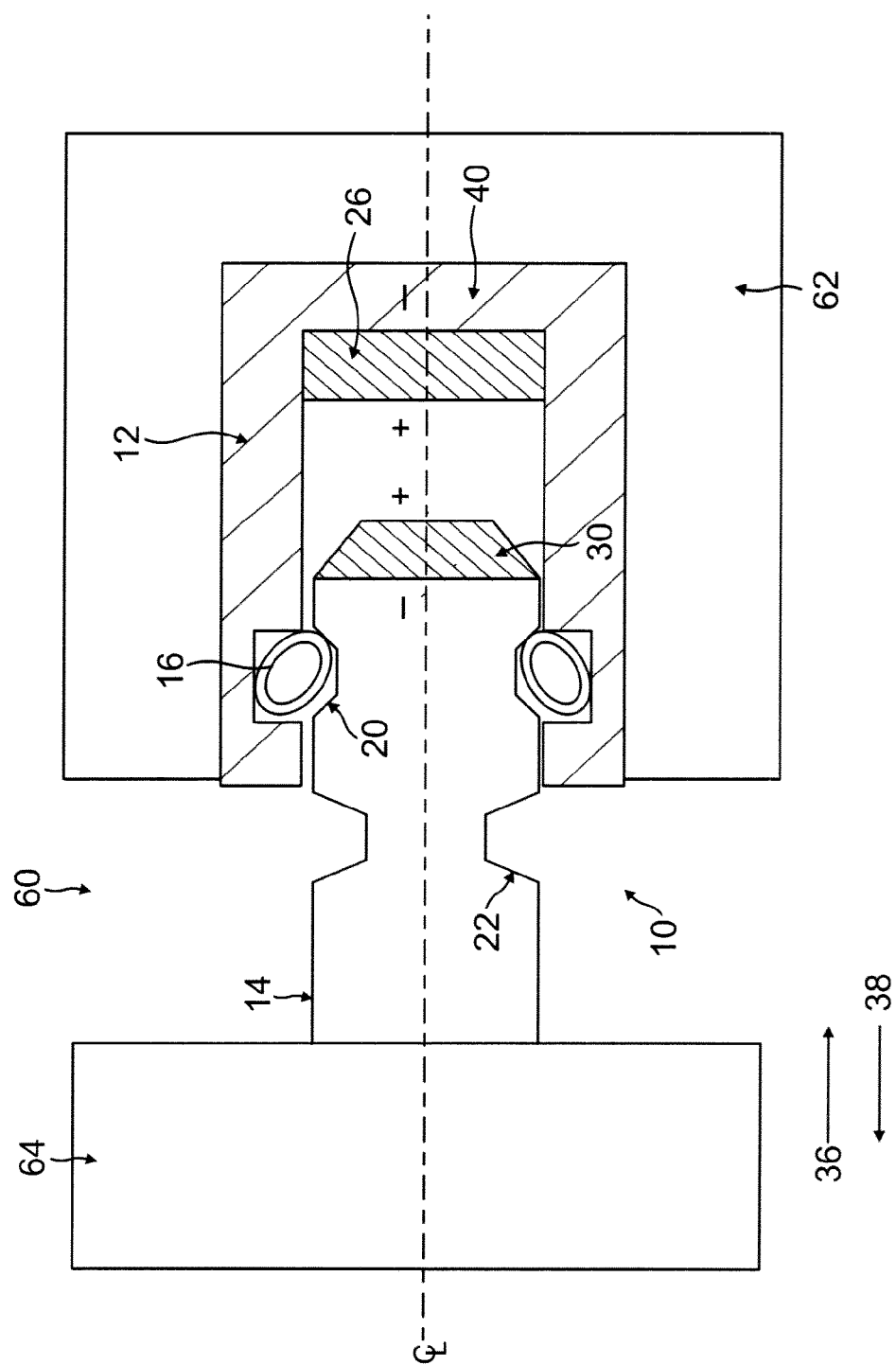
FIG. 1E is a schematic cross-section side view of the dual direction connector of FIG. 1A attached to first and second articles of manufacture.

FIG. 1E is a schematic side view of the connector 10 of FIGS. 1A-1D incorporated in or with an article of manufacture 60, which includes a first article section 62 and a second article section 64. FIG. 1E shows the article of manufacture 60 being latched in a first latched position, which limits retraction of the second connector component 14 in the second direction 38 but permit further insertion in the first direction 36 if the restriction feature 40 is overcome. In practice, the article of manufacture 60 may embody any number of different objects across any number of different industries and applications. As non-limiting examples, the connector 10 may be incorporated in various aerospace, military & defense, oil & gas, automotive, power transmission & distribution, medical device, industrial, medical electronics, green tech, and consumer industries. For example in the aerospace industry, the connector may be used, as non-limiting examples, as a replacement for a ball detent system on a fuel coupling connector, as a fastener for fastening access panels on aircraft to allow removal without tools, for holding injection seats on aircraft to allow removal for maintenance without tools, and for tethering a UAV (unmanned aerial vehicle) to a rail launch system, which allows for positive mechanical/electrical connection and release by allowing the spring to move to the second position. With reference to FIG. 1E, for example, a seat 64 may be incorporated with one or more second connector components 14 to be attached to a plane or foundation 62 having a corresponding number of first connector components 12, which comprise bores having a groove 18 for capturing a spring 16. In another example, the components are reversed so that the seat includes a plurality of first connector components 12 while the plane or deck includes a corresponding number of second connector components 14.

In another embodiment, the connector 10 of FIGS. 1A-1D is useable as a replacement for fasteners and bolts, which includes a nut/bolt combination or a screw/threaded bore combination. For example, the second connector component 14 may replace a bolt or a screw while the first connector component 12 may replace a nut or a threaded bore. The first article member 62 and the second article member 64 may embody any number of objects or devices that are typically used with a nut/bolt combination or a screw/threaded bore combination, for example a picture frame and a wall, a chair leg and a chair seat, a shelf and a case, etc.

For military and defense industry, the connector 10 may be used, as non-limiting examples, as an interconnect system for holding and quick replacement of modular Radar/LiDAR/Electro Optics/Infrared systems, as a fastener system for ground-based robotic vehicle, allowing quick replacement of different modules for varying applications, as a fastener for fastening access panels or armor plating on vehicles to allow removal without tools; and for tethering truck/vehicle mounted rockets/missiles providing positive mechanical/electrical connection, but also allowing for release at time of vehicle launch.

For oil and gas industry, the connector 10 may be used, as non-limiting examples, as a down-hole tool installation/retrieval system, for securing cables and wires for control systems, for opening and closing hatch doors, for securing shelves to hold supplies, and for anchoring machineries and devices to foundations and platforms.

For power transmission and distribution industry, the connector 10 may be used, as non-limiting examples, as a connector cable to replace the need for soldering, to secure control panels, to connect machineries and devices, to close cabinets and doors, and to secure objects together.

For medical device, medical electronics, automotive, industrial, and alternative energy industries, the connector 10 may be used, as non-limiting examples, as electrical connectors, as mechanical connectors, as fluid line connectors, and as electrical quick connectors.

Thus, an aspect of the present system and method is understood to include a connector comprising a first connector component having a first connector groove and a second connector component having a primary groove and a secondary groove, a restriction feature formed with the first connector component, the second connector component or both is incorporated to restrict movement of the first connector component along a first direction until the restriction is overcome, and a canted coil spring captured between the first connector groove and the primary groove to lock the first connector component to the second connector component in a first position. The connector is further understood to include a mechanism for overcoming the restriction feature to enable further movement of the first connector component along the first direction to a second position to capture the canted coil spring between the first connector groove and the secondary groove. In one example, the mechanism to overcome the restriction feature is an application of insertion force that is higher than opposing magnetic forces. The connector is further understood to permit rotation of a spring axis when in the second position. The connector is further understood to require progressively larger insertion force due to increasing opposing forces as the second connector component moves deeper into the bore of the first connector component. The connector is further understood to permit movement of the second connector component along a second direction which is opposite the first direction, after being in the second position. The connector is further understood to include retraction forces generated by the opposing magnetic forces. In a specific example, the first connector component is a housing comprising a bore and having the first connector groove located therein. In another example, the first connector component is a cylindrical member or pin having the first connector groove located on an outside surface. In yet another example, the restriction feature is embodied by at least one electromagnetic device that is controllable by electric signals.

The connector 10 may be made from a number of different materials, including from metal, plastic, and engineered plastic (such as PEEK and PEK) depending on the application. The metal may also be a composite and may including metal plating or deposition with highly conductive metallurgy, such as gold or copper, corrosion resistant material, and/or high tensile strength material, such as stainless steel The connector 10 may be used purely as a mechanical device to hold different components together and/or as an electrical connector for transferring electrical signals or current between components that are connected to the first connector component 12 and the second connector component 14. The spring 16 may be made from a single metal wire or from a multi-layer wire. Exemplary multi-layer wires are disclosed in application Ser. No. 12/767,421, Pub No. 2010/0289198, filed Apr. 26, 2010.

Figure 2A:
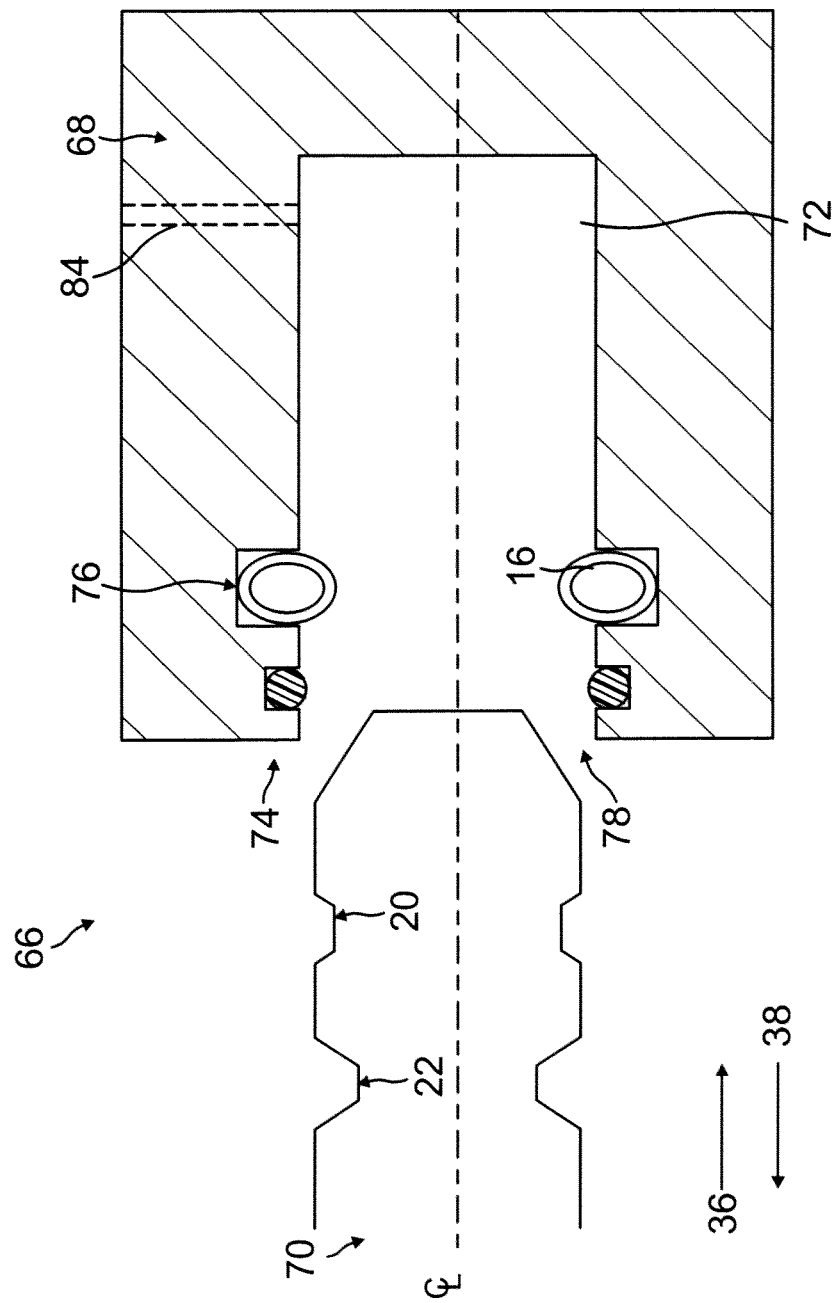
FIG. 2A shows a schematic cross-sectional side view of an alternative dual direction connector, which shows a second connector component aligned for insertion into a bore of a first connector component and a restriction feature provided to restrict movement of the first connector component within the bore.

FIG. 2A is a schematic cross-sectional side view of an alternative connector assembly, or simply connector, provided in accordance with aspects of the present device system and method, which is generally designated 66. As shown, the connector 66 comprises a first connector component 68 aligned to and configured to be inserted into a bore 72 of a second connector component 70, similar to the connector 10 of FIGS. 1A-1E. However, in the present embodiment, a modified restriction feature 74 is used, which comprises a seal for causing pressure build-up, such as air pressure, to restrict movement of the second connector component 70 in the first direction 36.

Figure 2B:
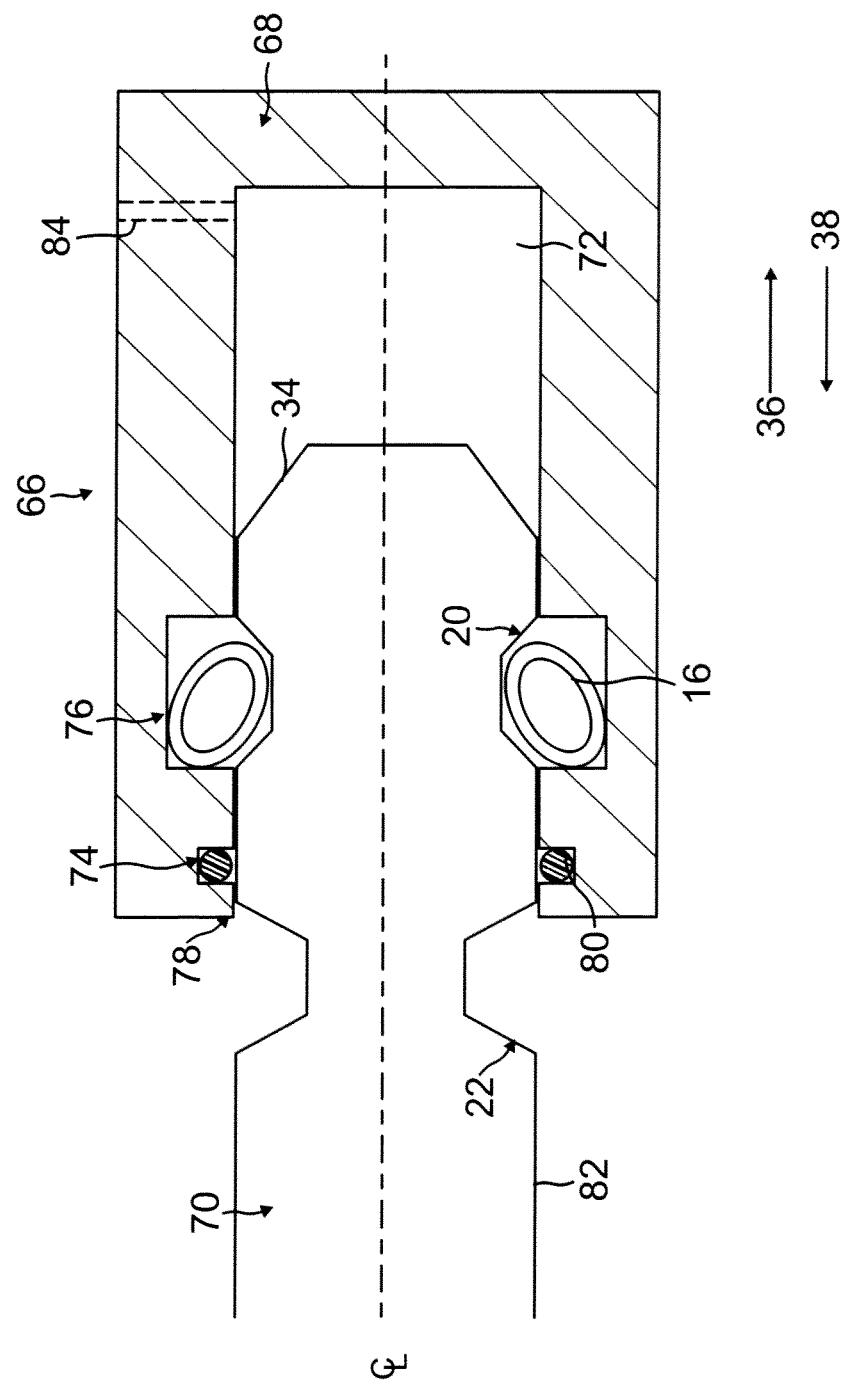
FIG. 2B shows a schematic cross-sectional side view of the dual direction connector of FIG. 2A with the first connector component and the second connector component latching a canted coil spring in a first latched position and loading the spring generally along a major axis.

With reference to FIG. 2B in addition to FIG. 2A, a seal groove 74 is incorporated adjacent the first connector groove 76. In the example shown, the seal groove 74 is located closer to the entrance or opening 78 of the first connector component 68 than the housing groove 76. In another example, the seal groove 74 is located distally of the housing groove 76 and further away from the entrance 78. A seal 80, such as an O-ring, is positioned in the seal groove 74 and configured to seal against the outside surface 82 of the second connector component 70. Thus, once the second connector component 70 is inserted into the bore 72 and advanced in the first direction 36 to move the connector to the first latched position shown in FIG. 2B, pressure builds up in the bore 72, similar to a hand bicycle pump, to resist movement in the first direction 36. A relief bore 84 may be incorporated in the first connector component 68 to control the amount of pressure build-up during the insertion process. In one example, the relief bore is sized with a single bore diameter. In another example, a spring loaded valve, such as a relief valve, may be incorporated with the relief bore 84 to release air or pressure from the bore 72 only upon reaching a certain selected pressure value.

Thus, the present connector 66 is understood to include a first connector component and a second connector component and wherein insertion of the first connector component into the second connector component to move the connector into a first latched position requires a sufficient insertion force in addition to a force that can overcome pressure, such as air pressure, generated by the restriction feature of the present device, assembly and method, which is a seal for pressure build-up in the decreasing bore during insertion. In a specific embodiment, a relief bore is provided in the first connector component to permit venting to minimize excessive pressure build-up in the bore of the first connector component. A spring actuated relief valve may be incorporated with the relief bore 84 to control the minimum pressure build-up in the bore 72 before the valve opens.

Figure 2C:
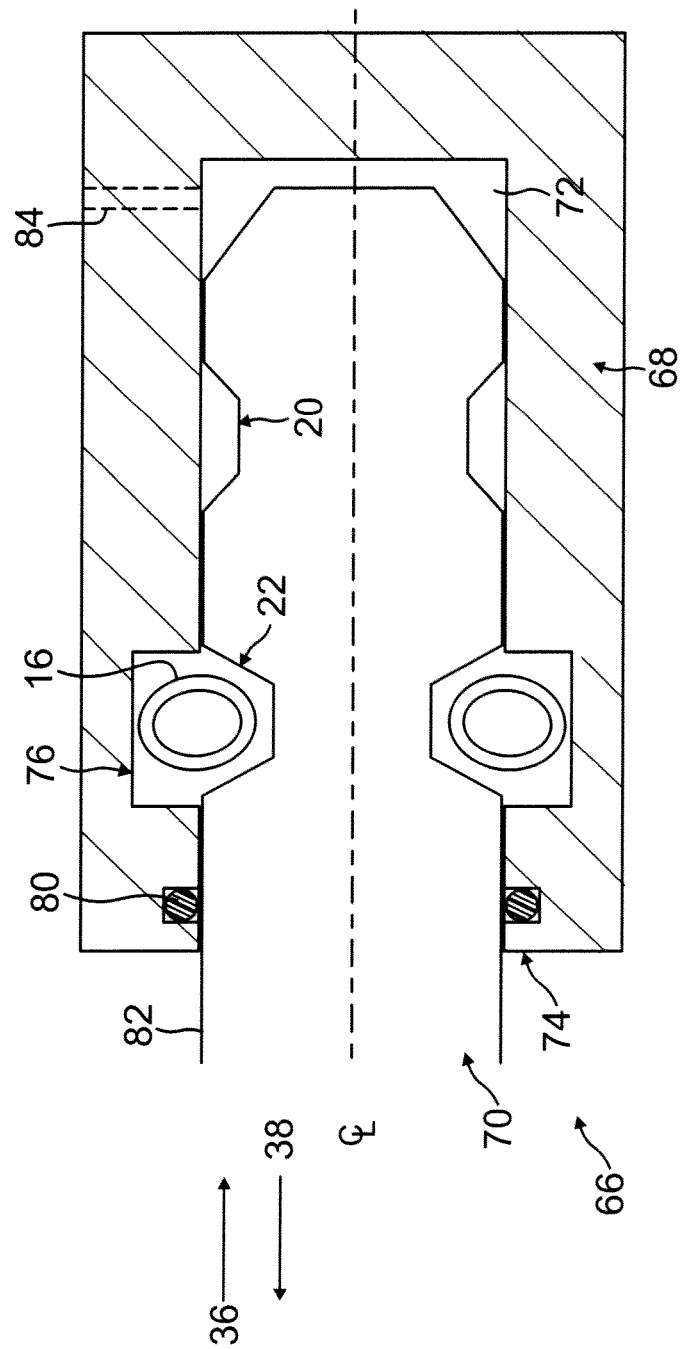
FIG. 2C shows a schematic cross-sectional side view of the dual direction connector of FIG. 2A with the first connector component latched in a second latched position with the second connector component and the pressure provided by the restriction feature overcome by an insertion force.

With reference now to FIG. 2C in addition to FIG. 2B, the second connector component 70 is shown inserted further into the bore 72 of the first connector component 68 to move the connector 66 to the second latched position. In this position, the spring 16 is allowed to relax and rotate from its first latched position due to the larger secondary groove 22. The seal 80 is also shown sealing the outside surface 82 of the second connector component 70. From this position, the connector can be disconnected.

To unlock the second connector component 70 from the first connector component 68, the second connector component 70 is moved in the second direction 38 by applying a retraction force that is sufficient to rotate the spring 16 and overcome the restriction feature 74. As previously described, the spring 16 is allowed to rotate and relaxes when captured by the secondary groove 22 due to its larger size relative to the primary groove 20. At this time, the second connector component 70 is free to move in the second direction 38 to separate from the first connector component 68. During this process, air is purged back into the bore 72 through the relief bore 84. A separate vent hole may be incorporated during the withdrawal process to break the vacuum in the bore 72, either with or without a vacuum relief valve. The spring 16 is moved with the second connector component 70 and returns to its first latched position but with the major axis of the spring 16 rotated, similar to the embodiment of FIG. 1D. Note that the reference first and second connector components are intended to designate different parts only and that the components can be reversed. In other words, the second connector component may be referred to as the first connector component and may incorporate a single external groove while the housing incorporates two internal grooves with one being the primary groove and the other being the secondary groove. The terms first direction and second direction are also relative terms and depend on which component is being move and which is being held stationary.

Similar to the connector 10 of FIGS. 1A-1E, the present connector 66 may be practiced in a wide variety of applications. As non-limiting examples, the connector 66 may be incorporated in various aerospace, military & defense, oil & gas, automotive, power transmission & distribution, medical device, industrial, medical electronics, green tech, and consumer industries. For example, the present connector 66 may be attached to first and second article sections or pieces as shown in FIG. 1E.

Thus, aspects of the present device, assembly and method include a connector 66 comprising a first connector component, a restriction feature, and a second connector component and wherein the restriction feature causes pressure fluctuations in the bore of the first connector component during movement of the second connector component in either a first direction or a second direction. The present device, assembly, and method are also understood to include a restriction feature that restricts but permits relative movement between the first connector component and second connector component when applying a moving force that can overcome pressure build-up inside a bore of the second connector component. In a specific example, the restriction feature is an O-ring positioned in a groove formed in or on either the first connector component or the second connector component (not shown). More generally, the present connector assembly is understood to permit venting outwardly through a port and venting inwardly through the port when moving the first and second connectors relative to one another.

Figure 3:
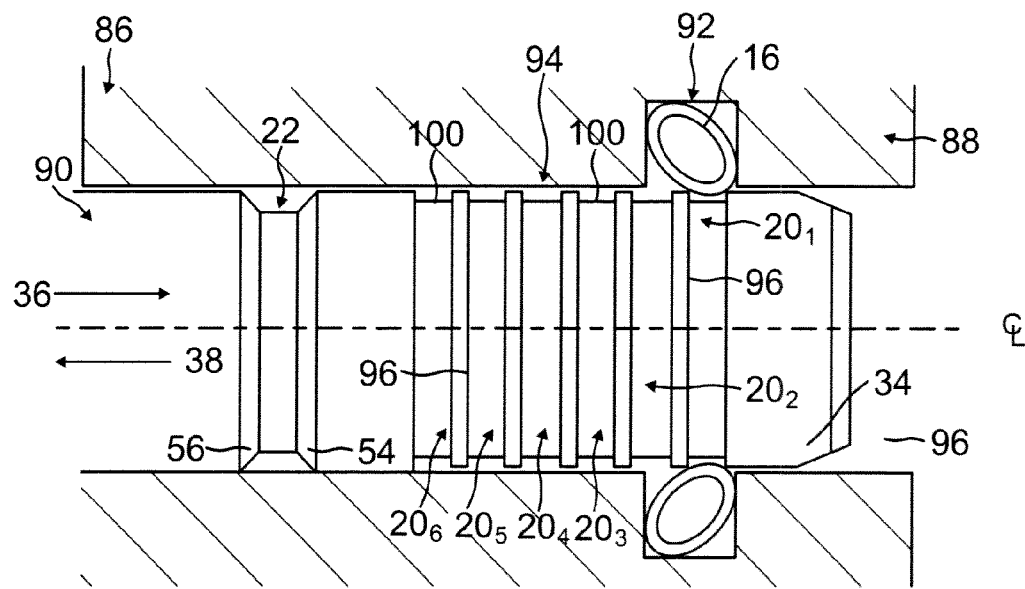
FIG. 3 shows a schematic cross-sectional side view of an alternative dual direction connector, which shows a second connector component located in a bore of a first connector component and a restriction feature in the form of a plurality of spaced apart grooves restricting further advancement until overcome by an insertion force.

FIG. 3 is a schematic side view of an alternative connector provided in accordance with aspects of the present device, system, and method, which is generally designated 86. As shown, the connector 86 comprises a first connector component 88 and a second connector component 90, which are locked to one another by capturing a canted coil spring 16 between the first connector groove 92 and the primary groove 20 on the second connector component 90. As previously discussed, in the locked position, the spring 16 is loaded along its major axis, i.e., its longer axis, so that separation by moving the second connector component 90 along the second direction 38, or moving the first connector component along the first direction 36, will require compressing the spring along its major axis, which normally does not compress. However, unlocking is permitted if the spring 16 is able to rotate so that it can then compress along its minor axis, i.e., its shorter axis. Note that when a particular sliding direction is discussed for a connector component, it is assumed that the other connector component is held stationary. Obviously, the components can be moved simultaneously or a different component is held stationary.

The connector 86 further includes a restriction feature 94 for restricting movement of the connector to a second latched position with the secondary groove 22 until the restriction feature is overcome. In one exemplary embodiment, the restriction feature 94 is a plurality of spaced apart primary grooves $20_1 \ldots 20_n$ with "n" designating a whole integer equaling the total number of primary grooves, which is six (6) in the present device and system. In other embodiments, the number of primary grooves is less than six while in some other embodiments it is more than six. The restriction feature may be viewed as a plurality of primary grooves $20_2 \ldots 20_n$ located between the first primary groove $20_1$ and the secondary groove 22. Thus, before the first connector component 88 and the second connector component 90 can move away from one another, the spring 16 must move through the plurality of spaced apart primary grooves $20_1 \ldots 20_n$ to then move to the second latched position of the secondary groove 22 to rotate. As the spring 16 latches between the first connector groove 92 and each of the plurality of primary grooves $20_1 \ldots 20_6$, the spring 16 is loaded along its major axis as shown in FIG. 3 and prevents the second connector component 90 from moving in the second direction 38. Once moved to the second latched position (not shown) and captured by the secondary groove 22 and the housing groove 92, the spring is allowed to relax and rotate due to the larger secondary groove, as previously discussed. At this point, the second connector component 90 can move in the second direction 38 to move the spring 16 back to the first latched position (similar to FIG. 1D) through the plurality of spaced apart primary grooves $20_2 \ldots 20_6$.

After the successive unlatching through the plurality of spaced apart primary grooves $20_1 \ldots 20_6$ during retraction, the second connector component 90 can now completely separate from the first connector component 88 and the bore 96.

As shown, each of the spaced apart primary grooves $20_1 \ldots 20_6$ are separated from one another by a ring or flange 98. The ring or flange 98 also functions as side walls for the various primary grooves $20_1 \ldots 20_6$. In one example, each of the spaced apart primary grooves comprises two side walls 98 and a bottom wall 100. As shown, the two side walls 98 are generally parallel to one another and orthogonal to the bottom wall 100, which has a flat bottom. In other embodiments, the primary grooves can have tapered wall surfaces, such as a tapered sidewall and/or a tapered bottom wall. The secondary groove 22 preferably has the same groove configuration as the secondary groove 22 discussed above with reference to FIGS. 1A-1D including optionally having a V-groove configuration.

Like the embodiment of FIGS. 1A-2C, the present connector 86 may be attached to a first article of manufacture and/or a second article of manufacture to enable removable connection between the two articles of manufacture.

Thus, aspects of the present device, system, and method include a first connector component and a second connector component. The first connector component comprising a groove or a combination primary groove spaced from a secondary groove and the second connector component comprising the other one of the groove or the combination primary groove spaced from a secondary groove. The connector further comprising a first spring position defined by the groove and the primary groove capturing a canted coil spring and loading the canted coil spring along a first spring angle to permit moving the second connector component in a first direction but not in a second opposite direction relative to the first connector component. In one example, the first direction is restricted by a restriction feature that can be overcome through application of force in the first direction. In a specific example, the restriction feature is a plurality of primary grooves located between the first primary groove and the secondary groove. The restriction feature presents a restriction against movement of the second connector component in the first direction but can be overcome by applying a series of successive insertion force through the plurality of subsequent primary grooves $20_2 \ldots 20_n$. Once the spring moves through the last of the primary grooves, the first connector component and the second connector component may move relative to one another to move the spring to a second spring position which is a position in which the groove and the secondary groove captures the spring and allows the spring to rotate to a different spring angle than when in the first position. The spring is allowed to rotate due to the larger secondary groove, which is larger than all individual primary grooves $20_1 \ldots 20_n$. At the second spring position, the spring is able to rotate when the second connector component 90 is moved in the second direction 38 relative to the first connector component 88. In particular, the tapered side wall 54 of the secondary groove 22 contacts and rotates the spring 16 during movement of the second connector component 90 in the second direction 38 to separate from the first connector component.

Figure 4:
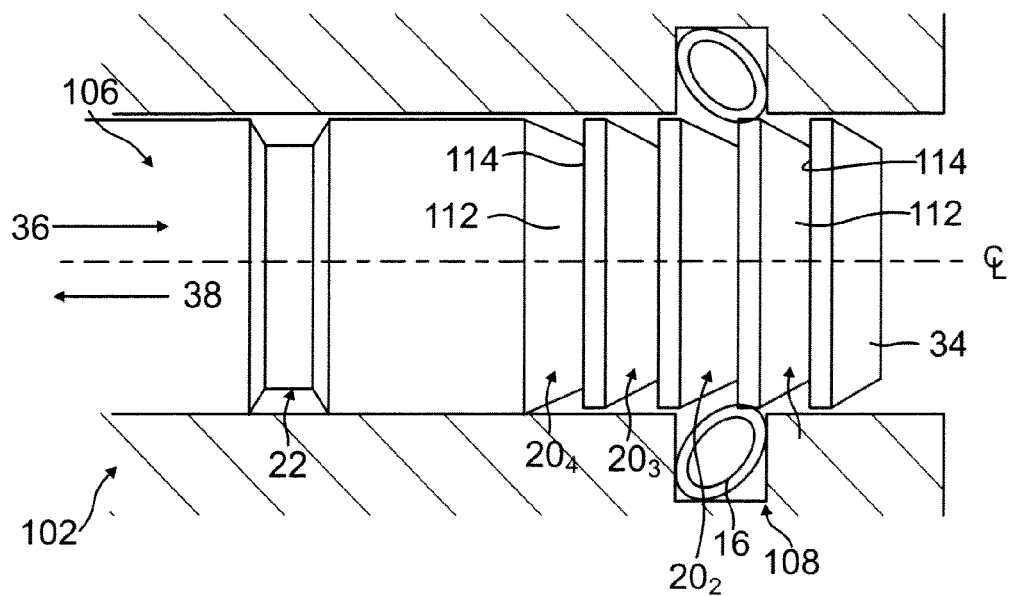
FIG. 4 shows a schematic cross-sectional side view of an alternative dual direction connector, which shows a second connector component located in a bore of a first connector component and a restriction feature in the form of a plurality of spaced apart grooves restricting further advancement until overcome by an insertion force. The plurality of spaced apart grooves differs in groove geometry compared to the grooves of FIG. 3.

FIG. 4 is a side view of yet another connector assembly provided in accordance with aspects of the present device, system, and method, which is generally designated 102. Like the other connector assemblies and devices discussed elsewhere herein, the present connector assembly has two latched positions and wherein a restriction feature is provided to control movement between the first latched position and the second latched position. In the present embodiment, the connector assembly 102 comprises a first connector component 104 comprising a first connector groove 108 and a second connector component 106, which has a primary groove 20 and a secondary groove 22 similar to the connector assemblies discussed with reference to FIGS. 1A, 2A and 3. In the present connector 102, more like the connector assembly 86 of FIG. 3, the second connector component 106 comprises a plurality of primary grooves $20_1 \ldots 20_n$, where "n" represents a whole integer equaling to the total number of primary grooves. In one specific embodiment, the first connector component 106 comprises four (4) primary grooves $20_1 \ldots 20_n$, which may alternatively be viewed as having a plurality of primary grooves $20_2 \ldots 20_n$ located in between the first primary groove $20_1$ and the secondary groove 22. In other embodiments, the number of primary grooves may be less than four or greater than four, depending on the desired application, such as depending on the depth of insertion before allowing the spring to move to the second latched position.

The connector 102 of FIG. 4 has a first latched position and a second latched position and a plurality of additional latched positions therebetween provided by the restriction feature 110, which in the present embodiment, like the embodiment of FIG. 3, is a plurality of primary grooves $20_2 \ldots 20_n$. However, unlike the connector 86 of FIG. 3, the plurality of primary grooves $20_1 \ldots 20_n$ each has a tapered bottom wall 112, which is tapered relative to a centerline of the second connector component 106. Each groove also has at least one side wall 114, which may be tapered but preferably orthogonal to the centerline of the second connector component. The connector 102 is otherwise usable in the same manner as described above with reference to the connector 86 of FIG. 3.

In practice, the connector 102 may be used with first and second articles of manufacture to secure the two articles of manufacture together, similar to other connectors discussed elsewhere herein. Furthermore, movement of the various connector components or connector pieces may be done automatically, such as using a servo motor with gears or a linkage system, using electromagnetic force, fluidic force, and/or pneumatic pressure.

Figure 5A:
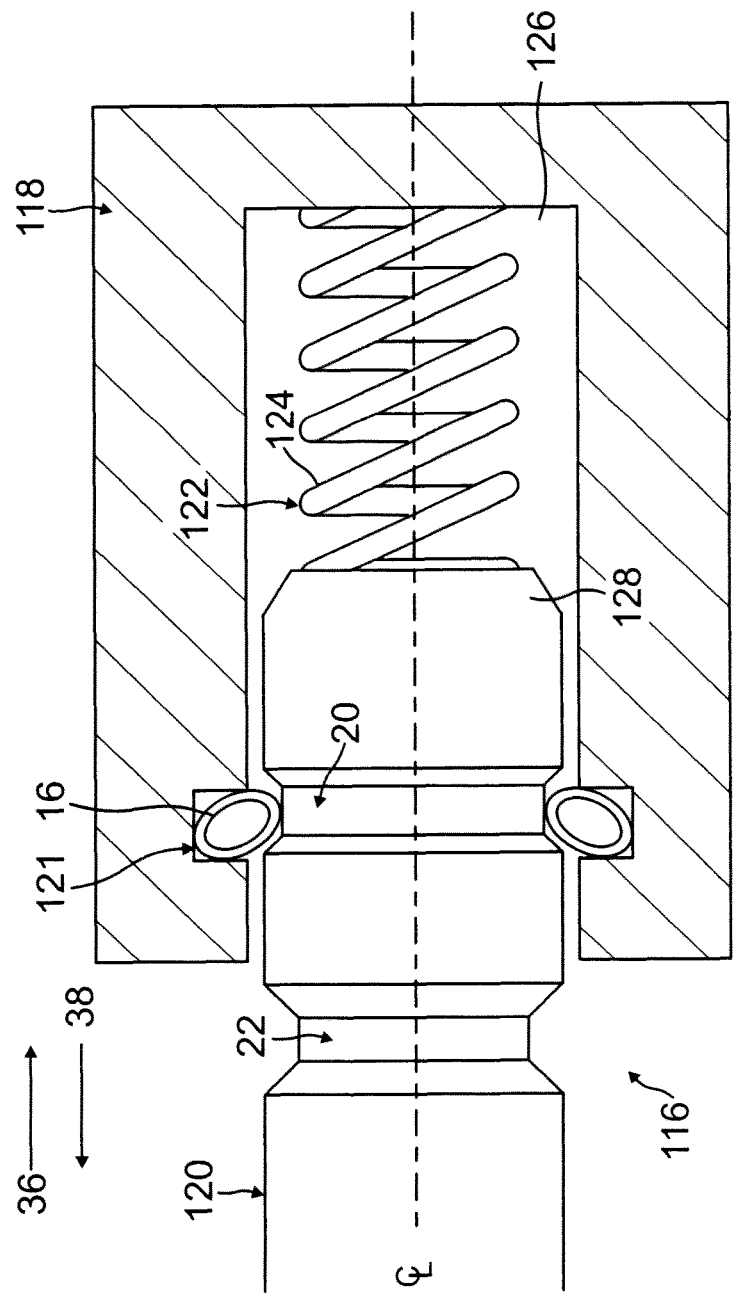
FIG. 5A shows a schematic cross-sectional side view of an alternative dual direction connector, which shows a second connector component located in a bore of a first connector component and a restriction feature restricting further advancement.

FIG. 5A is a cross-sectional side view of yet another connector assembly provided in accordance with aspects of the present device, system, and method, which is generally designated 116. Like the other connector assemblies and devices discussed elsewhere herein, the present connector assembly has two latched positions and wherein a restriction feature is provided to restrict movement between the first latched position and the second latched position. As shown, the connector 116 comprises a first connector component 118 and a second connector component 120, which are engaged to one another in the first latched positioned (FIG. 5A) by moving the second connector component 120 in the first direction 36. In the first latched position, the spring 16 is loaded along its major axis by the first connector groove 121 and the primary groove 20, which prevents the second connector component 120 from retracting in the second direction 38.

In the present embodiment, a restriction feature 122 comprising a helical coil spring 124 is incorporated with the first connector component 118 to restrict further insertion of the second connector component 116 into the bore 126. The spring 124, the configuration of the bore 126 and/or the nose section 128 of the second connector component 120 may be selected so that the spring and the second connector component do not abut or touch until the first latched position, as shown in FIG. 5A. In another example, the spring 124 and the second connector component 120 can abut or touch just before the first latched position or after, when the second connector component 120 is further inserted into the bore 126.

Figure 5B:
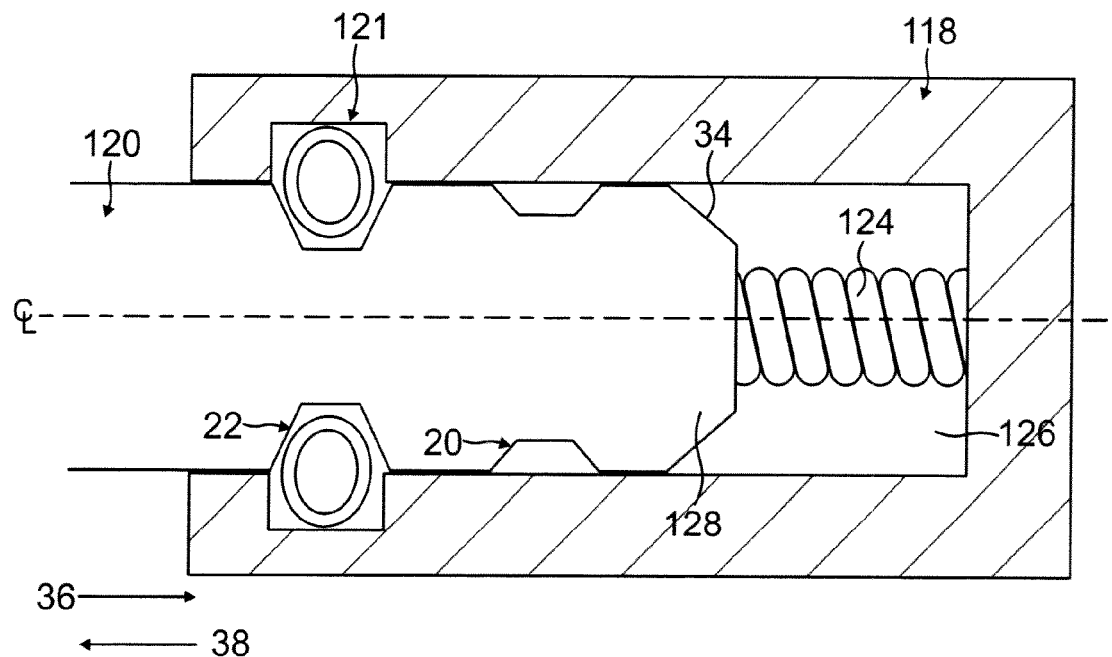
FIG. 5B shows a schematic cross-sectional side view of the dual direction connector of FIG. 5A with the first connector component engaged to the second connector component in a second latched position after overcoming the restriction force generated by the restriction feature.

FIG. 5B is a cross-sectional side view of the connector of FIG. 5A in the second latched position. As shown, the second connector component 120 is advanced further into the bore 126 and compresses the spring 124 to overcome the restriction presented by the spring 124. In the second latched position, the canted coil spring 16 is allowed to rotate due to the relatively larger secondary groove 22. The second connector component 120 can now be removed from the first connector component 118 by moving in the second direction 38. During this movement in the second direction 38, the restriction spring expands 124 and facilitates retraction of the second connector component 120 away from the first connector component. In practice, the connector assembly 116 may be used with first and second articles of manufacture to secure the two articles together, similar to other connectors discussed elsewhere herein.

In one example, the restriction spring 124 is selected to have a linear spring constant so that further insertion by the second connector component 120 into the bore 126 of the first connector component 118 requires a constant force. However, the spring may be selected with a variable spring constant to require progressively greater insertion force or progressively less insertion force. For example, the spring may have wires of different diameters or metallurgy or may have two or more different springs with different spring constants interconnected together.

Thus, the present connector may be understood to include a first connector component and a second connector component having a first latched position and a second latched position and wherein the connector is restricted from moving from the first latched position to the second latched position by a restriction feature. The connector is further understood to permit latching in the second latched position only after overcoming the restriction feature. In one embodiment, the restriction feature is overcome by applying an insertion force that is greater than a spring force of a fixed spring constant. In another example, the spring constant is variable. Thus, broadly speaking, the connector assembly comprises multi-latch points with at least one restriction feature between the multi-latch points. In a specific embodiment, the restriction feature is a helical coil spring.

Figure 5C:
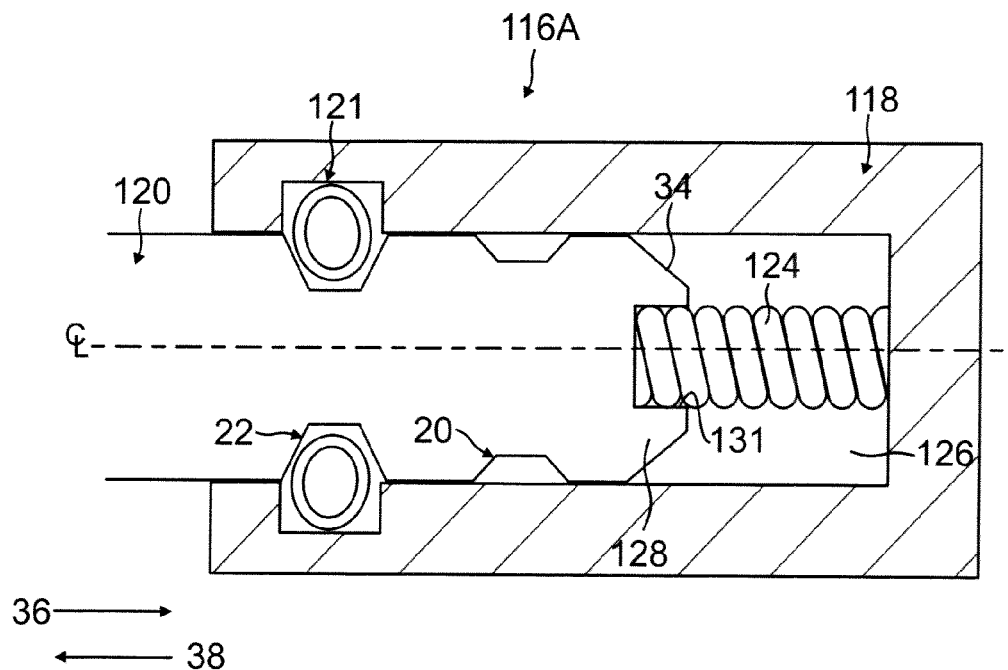
FIG. 5C shows a schematic cross-sectional side view of an alternative dual direction connector, which varies the second connector component of FIGS. 5A and 5B.

FIG. 5C is a cross-sectional side view of yet another connector assembly provided in accordance with aspects of the present device, system, and method, which is generally designated 116A. The connector assembly 116A is similar to the connector assembly 116 of FIGS. 5A and 5C with the exception of a recessed nose section or counter-bore 131 for receiving the spring 124. The counter-bore 131 facilitates alignment with the spring 124 in the event of an axis force being applied by the second connector component against the spring and to prevent the spring from deflecting during its compression.

Figure 6A:
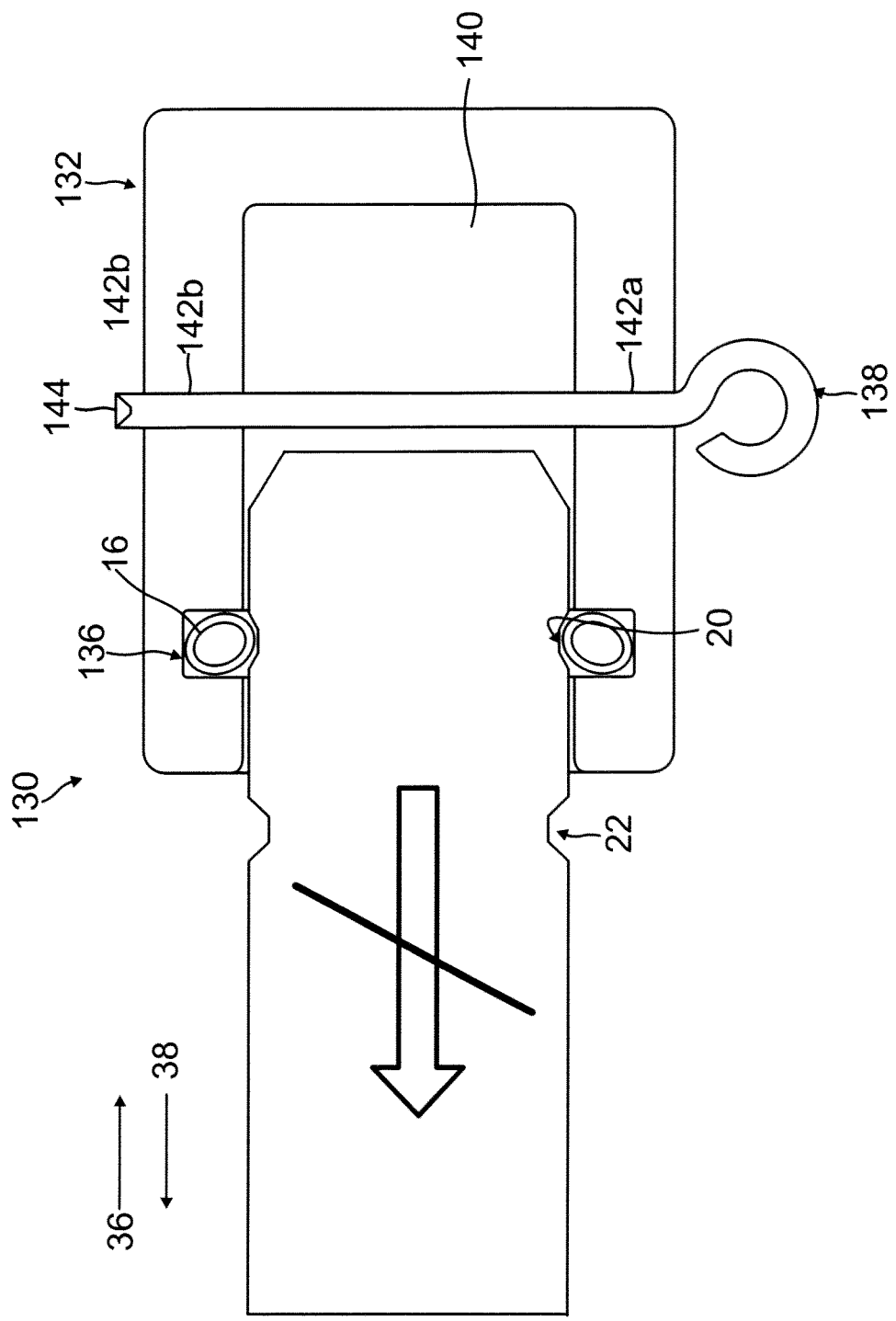
FIG. 6A shows a schematic cross-sectional side view of an alternative dual direction connector, which shows a second connector component located in a bore of a first connector component and a restriction feature restricting further advancement until overcome.

FIG. 6A is a schematic cross-sectional side view of an alternative connector assembly provided in accordance with aspects of the present devices, systems, and methods, which is generally designated 130. As shown, the connector 130 comprises a first connector component 132 and a second connector component 134, which are locked to one another by capturing a canted coil spring 16 between the first connector groove 136 and the primary groove 20. As previously discussed, in the locked position, the spring 16 is loaded along its major axis, i.e., its longer axis, so that separation by moving the second connector component 134 along the second direction 38, or moving the first connector component along the first direction 36, will require compressing the spring along its major axis, which normally does not compress without destroying the spring. However, unlocking is permitted if the spring 16 is able to rotate so that it can then compress along its minor axis, i.e., its shorter axis, to permit moving the second connector component 134 along the second direction 38. Note that when a particular sliding direction is discussed for a connector component, it is assumed that the other connector component is held stationary. Obviously, the components can be moved simultaneously or a different component is held stationary.

The connector 130 further includes means for restricting relative movement between the first connector component 132 and the second connector component 134 to prevent the spring 16 from rotating. In the present embodiment, the means for limiting relative movement is a shear pin 138, which acts as a restriction feature to prevent the second connector component 134 from sliding further into the bore 140 of the first connector component 132. As shown, the shear pin 138 is inserted into a pair of bosses 142 on the first connector component 132 and removably held thereto to act as a restriction feature for the second connector component 134. In an example, the shear pin 138 is engaged to the bosses 142*a*, 142*b* using tapered fitting. In another example, the secure pin 138 is held using a cap or a bolt (not shown) to secure against the pin end 144. In still another example, the pin end 144 is threadedly engaged to the boss 142*b*. Although the end 146 of the second connector component 134 is shown spaced from the shear pin 138, a smaller gap than shown or no gap may be incorporated to restrict relative movement between the two connector components until the shear pin 106 is sheared by the insertion force of the second connector component 134.

Figure 6B:
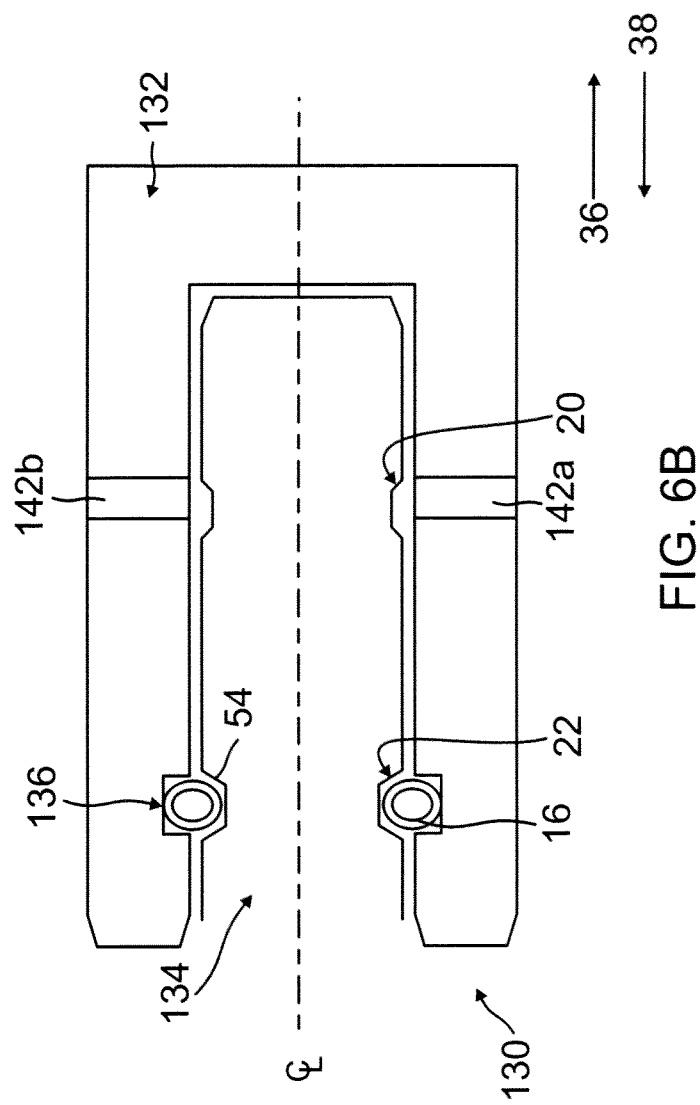
FIG. 6B shows a schematic cross-sectional side view of the dual direction connector of FIG. 6A with the second connector component further into the bore of the first connector component in a second latched position after overcoming the restriction provided by the restriction feature.

FIG. 6B is a schematic cross-sectional side view of the connector 130 of FIG. 6A, shown with the shear pin 106 removed from the first connector component 132 and the second connector component 134 advanced further into the bore 140 of the first connector component to move the spring 16 into a second latched position from the first latched position (FIG. 6A). By removing the shear pin, it is understood that the pin is either sheared by the advancing force or is physically removed from the holding bosses. In the second position, the spring 16 is captured by the first connector groove 136 and the secondary groove 22 of the second connector component. As shown, the spring 16 is allowed to rotate so that its major axis is generally vertical. i.e., generally perpendicular to the centerline of the second connector component 134. This rotation is made possible at least in part by providing a larger secondary groove 22 than the primary groove 20, which is understood to mean wider, deeper, or both wider and deeper. The larger secondary groove 22 allows the spring 16 to rotate to its more relaxed position. From this second spring position (FIG. 6B), the second connector 134 can move in the second direction 38 relative to the first connector component 132 to separate therefrom. The spring is preferably an axial canted coil spring. In another example, the spring is a radial canted coil spring.

The shear pin 138 is configured to snap, shear, or break when the second connector component 134 is advanced against the pin 138 (FIG. 6A) and overcomes the shear strength of the pin. The shear strength can be selected for a desired application by selecting the material type and/or size, such as a desired pin diameter to shear at a certain value.

Like the embodiment of FIG. 1E, the present connector 130 may be attached to a first article of manufacture and/or a second article of manufacture to enable removable connection between the first and the second articles of manufacture.

Thus, aspects of the present device, system, and method include a first connector component and a second connector component. The first connector component comprising a groove or a combination primary groove spaced from a secondary groove and the second connector component comprising the other one of the groove or the combination primary groove spaced from a secondary groove. The connector further comprising a first spring position defined by the groove and the primary groove capturing a canted coil spring and loading the canted coil spring along a first spring angle to permit moving the second connector in a first direction but not in a second opposite direction relative to the first connector component. In one example, the first direction is restricted by a restriction feature. In a specific example, the restriction feature is a shear pin engaged to the first connector component. The shear pin presents a restriction for the second connector component that can be overcome by movement of the second connector component along the first direction to shear the pin, or by removing the pin. At this time, the first connector component and the second connector component may move relative to one another to move the spring to a second spring position or second latched position, which is a position in which the groove and the secondary groove capture the spring but allow the spring to rotate to a different spring angle than when in the first position. At the second spring position, the spring is able to rotate when the second connector component 134 is moved in the second direction 38 relative to the first connector component 132. In particular, the tapered side wall 54 of the second groove 22 contacts and rotates the spring 16 during movement of the second connector component 134 in the second direction 38 to separate from the first connector component.

Figure 7:
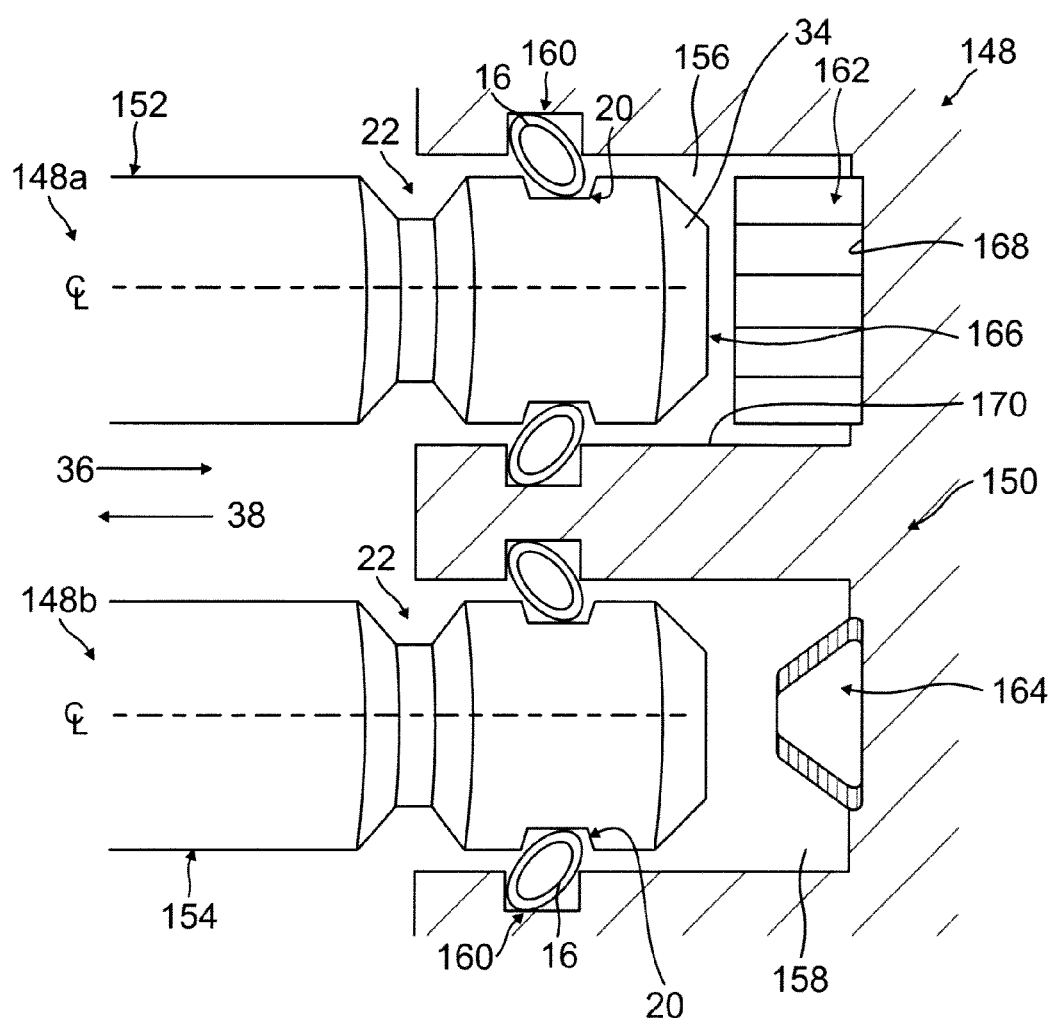
FIG. 7 shows a schematic cross-sectional side view of an alternative dual direction connector, which shows two second connector components located in two bores of a first connector component and a restriction feature in each bore restricting further advancement of the two first connector components until overcome.

FIG. 7 is a cross-sectional side view of yet another connector assembly provided in accordance with aspects of the present device, system, and method, which is generally designated 148. Like the other connector assemblies and devices discussed elsewhere herein, the present connector assembly has two parallel connected second connector components latched to a first connector component having two receiving bores and wherein the assembly has two latched positions. Also like the other assemblies, a restriction feature is provided to control movement between the first latched position and the second latched position. As shown, the connector assembly 148 comprises a first connector component 150 and two second connector components 152, 154, which engage the first connector component in respective first latched positions by moving the second connector components 152, 154 in the first direction 36. The two canted coil springs 16 in the two bores 156, 158 are loaded generally along their major axes in the first connector grooves 160 and the primary groove 20 on each of the second connector components 152, 154. As loaded, the second connector components 152, 154 cannot separate from the first connector component 150 by moving in the second direction 38.

The connector assembly 148 is further discussed below with reference to the upper connector assembly 148*a*, such as with reference to the second connector component 152 and the upper bore 156 of the first connector component 150 but is understood to apply equally to the lower connector component assembly 148b, such as to the second connector component 154 and the lower bore 158. However, the restriction features 162, 164 for the two different bores 156, 158 will be discussed separately as they differ. Additionally, while the first connector component 150 is shown with two integrally formed bores 156, 158 that are unitarily formed, they may be separately formed and subsequently attached or practiced as spaced apart distinct upper and lower units.

To move the upper connector assembly 148a to a second latched position to then permit separation of the second connector component 152 from the first connector component 150, the first connector component 152 has to overcome the restriction feature 162 to advance in the first direction 36 and further into the bore 156. In the example shown, the restriction feature 162 is a collapsible or deflectable structure that is crushed or moved out of the way by the advancing second connector component 152. For example, the structure can be a hollow tube designed with a certain crushed value, a honeycomb structure that crumbles under a certain compressive force, or a pivot member, such as a leaf spring or spring loaded pivotable beam, that moves out of the way when forced by the nose section 166. The restriction feature can also be a foam or foam-like material or a compressible rubber. The restriction feature 162 is mounted to the rear wall 168 of the bore 156 and/or to the sidewall 170 of the bore and may include weakened sections, such as frangible sections or kinked sections, to facilitate crumpling or crushing.

Once the restriction feature 162 is overcome, the second connector component 152 can advance and move the spring 16 to its second latched position (not shown but similar to FIG. 1C) to then rotate to its more relaxed position. At this point, the second connector component can reverse in the second direction 38 and return the spring to its first latched position, but with a rotated spring angle, similar to the angle shown with reference to FIG. 1D. The second connector component 152 can now completely separate from the first connector component 150 by continuing its movement in the second direction 38.

The restriction feature 164 for the lower connector assembly 148b is tapered or cone shaped. In one example, the restriction feature 164 is a conical compression spring. In another example, the restriction feature 164 is a cone shape hollow body, such as a metallic cone, designed with a certain crushed value. In still yet another example, the restriction feature is a cone shaped telescoping member having several cone sections that are mechanically engaged to one another. In still yet another example, the restriction feature is a Bellville washer or a wave spring. The lower connector assembly 148b can operate in a similar manner as the upper connector assembly 148a.

Thus, an aspect of the present connector is understood to include first and second connector components that have a first latched position and a second latched position using a canted coil spring and wherein movement between the two positions includes crushing or deflecting a restriction feature to advance the second connector component relative to the first connector component. The connector is also understood to permit complete separation of the second connector component from the first connector component by moving the spring to a second latched position so that it can rotate, but only after crushing or deflecting a restriction feature. Thus, broadly speaking, the connector comprises multi-latch points with at least one crushable or deflectable feature that must be activated between the multi-latch points. The present assembly is further understood to include a first connector component comprising two bores for receiving two different second connector components.

In practice, the connector assembly 148 may be used with first and second articles of manufacture to secure the two articles together, similar to other connectors discussed elsewhere herein. The first article of manufacture may be connected to both second connector components 152, 154. If so, one of the restriction features 162 or 164 may be omitted as the remaining restriction feature still needs to be overcome to move the connector assembly 148 from the a latched position to a second latched position.

FIG. 8A is a cross-sectional side view of yet another connector assembly provided in accordance with aspects of the present device, system, and method, which is generally designated 172. Like the other connector assemblies and devices discussed elsewhere herein, the present connector assembly has two latched positions and wherein a restriction feature is provided to control movement between the first latched position and the second latched position. As shown, the connector 172 comprises a first connector component 174 and a second connector component 176 that are similar in all aspects as previously described connector assemblies with the following exceptions. In the present assembly, the restriction feature 178 is a combination mechanical and electrical device. In one specific example, the restriction feature 178 is a switch or trigger 179 comprising a wire 180 that is connected to a controller or system (not shown). With reference to FIG. 8B in addition to FIG. 8A, when the second connector component 176 is advanced further into the bore 182 of the first connector component 174 to then enable separation, the circuit of the switch or trigger 179 closes and a signal is sent to the controller or system (not shown) to sound an alarm or indicator that the connector assembly 172 is activated and ready to be disconnected, i.e., separation of the second connector component from the first connector component. The connector assembly 172 with the trigger or switch 179 is usable in places like the airport or other controlled environments where separation of the connector would trigger an alarm. Thus, the second connector component 176 may be attached to an article of manufacture, such as to a door, and the first connector component 174 may be attached to another article of manufacture, such as to a door frame, so that when the two articles of manufacture are separated from one another, an alarm or indicator would trigger. Thus, in the present embodiment, the restriction feature is an alarm.

Figure 9A:
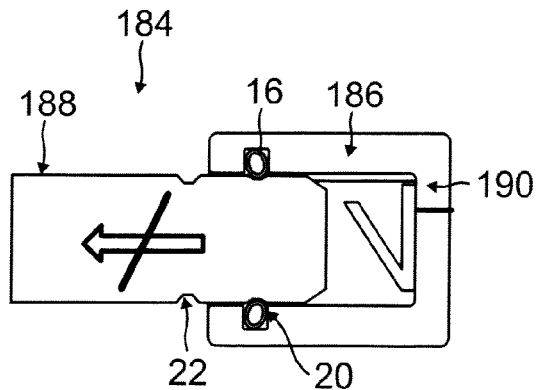
FIG. 9A shows a schematic cross-sectional side view of an alternative dual direction connector, which shows a second connector component located in a bore of a first connector component and a restriction feature embodying an alternative switch.
Figure 9B:
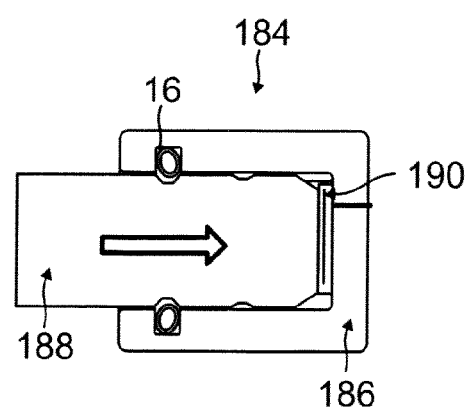
FIG. 9B shows a schematic cross-sectional side view of the connector with the switch in an activated position.

FIG. 9A is a cross-sectional side view of yet another connector assembly provided in accordance with aspects of the present devices, systems, and methods, which is generally designated 184. Like the other connector assemblies and devices discussed elsewhere herein, the present connector assembly has two latched positions and wherein a restriction feature is provided to control movement between the first latched position and the second latched position. The connector assembly 184 comprises a first connector component 186 and a second connector component 188 and is very similar to the connector assembly of FIGS. 8A and 8B. In the present connector assembly 184, the restriction feature 190 is a normally open (NO) contact switch that is configured to close when depressed by the nose section of the second connector component 188, as shown in FIG. 9B. In other embodiments, the switch is a magnetic switch, a single pole, single throw switch (SPST), a single pole, double throw switch (SPDT), a double pole, single throw switch (DPST), or a double pole, double throw switch (DPDT). However, other switch types are contemplated provided it incorporates movement of a second connector component relative to a first connector component with a canted coil spring for latching the two connector components and to activate the switch.

Figure 10A:
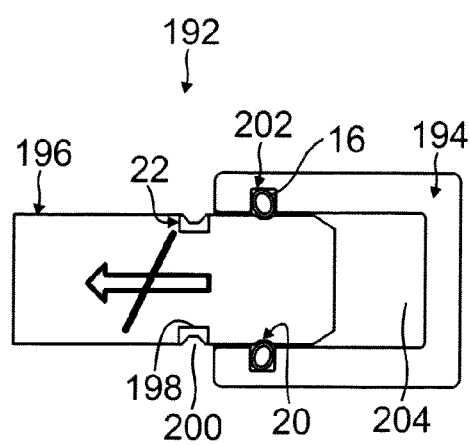
FIG. 10A shows a schematic cross-sectional side view of an alternative dual direction connector, which shows a second connector component located in a bore of a first connector component in a first latched position and an electrical circuit that is in an open state.

FIG. 10A shows a cross-sectional side view of yet another connector assembly provided in accordance with aspects of the present device, system, and method, which is generally designated 192. Like the other connector assemblies and devices discussed elsewhere herein, the present connector assembly has two latched positions and wherein a restriction feature (not shown) is provided to control movement between the first latched position and the second latched position. The restriction feature may be any of the features discussed elsewhere herein. As shown, the connector 192 comprises a first connector component 194 and a second connector component 196 that are similar in all aspects as previously described connector assemblies with the following exceptions. In the present assembly, the second connector component 196, including the primary groove 20, is made from a non-conductive material, such as from an engineered plastic, e.g., PEEK, PEK, PSU, ABS, PC, or PA, and comprises an annular ring 198 where a secondary groove is normally located. A conductive section or insert 200 is disposed in the annular ring 198 to form a secondary groove, which has similar groove configuration as other secondary grooves 22 discussed elsewhere herein. Alternatively, the second connector component is made from a conductive material and the first connector component is made from a non-conductive material.

The first connector component 194 may be made from a conductive material or a non-conductive material. If from a metallic material, the canted coil spring 16 is in electrical communication with the first connector groove 202 of the first connector component. If not from a conductive material, a wire or a conductive ring (not shown) may be incorporated with the first connector component 194 to be in electrical communication with the spring 16.

Figure 10B:
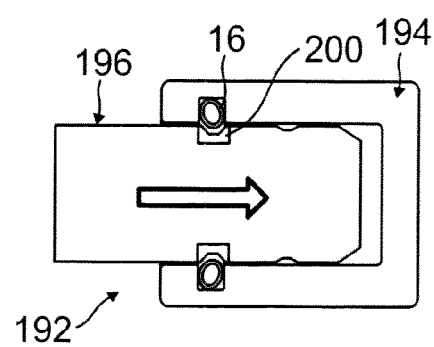
FIG. 10B shows a schematic cross-sectional side view of the dual direction connector of FIG. 10A with the second connector component located further in the bore of the first connector component in a second latched position and the electrical circuit closed by the contact between the spring and the secondary groove.

With reference to FIG. 10B, when the second connector component 196 is further inserted into the bore 204 of the first connector component 194, a closed loop is made between the conductive section 200, the spring 16, and the conductive portion of the first connector component. Thus, the connector assembly 192 can function as a switch or electrical trigger. In another example, a wire or cable (not shown) is incorporated with the second connector component 196 and in electrical communication with the conductive section 200. The wire or cable (not shown) can be connected to an electrical node located in an attached article of manufacture (not shown). The first connector component 194 may similarly be attached to another article of manufacture, similar to the embodiment of FIG. 1E.

FIG. 11 is a schematic process flow diagram depicting a method of use of a connector assembly provided in accordance with aspects of the present method, which is generally designated 206. The method comprises the steps of providing a first connector component and a second connector component, such as a housing and a pin, at step 208. Either the first connector component can comprise a groove or spaced apart primary and secondary grooves or the second connector component can comprise the other one of the single groove or spaced apart primary and secondary grooves. The process further includes inserting the second connector component in a first direction until a canted coil spring is latched between the groove and the primary groove in a first latched position at step 210. At step 212, a restriction feature is overcome by an insertion force to permit further insertion of the first connector and second connector components toward one another. The restriction feature can be any of the various features discussed elsewhere herein, including an alarm to restrict further movement.

The process further includes moving the connector assembly to a second latched position where the spring is latched between the groove and the secondary groove at step 214. The process further includes moving the second connector component in a second direction at step 216 to move the spring back to its first latched position but with a different spring angle. The second connector component can now separate from the first connector component. Although not shown, the connector assembly may be connected to at least one article of manufacture. Note that while the disclosed sequence is provided with specificity, it can be practiced in a different order than described.

FIG. 12 is a schematic process flow diagram depicting a method of manufacturing a connector assembly provided in accordance with aspects of the present method, which is generally designated 218. The method comprises the steps of forming a first connector component comprising a groove or a primary groove spaced form a secondary groove at step 220. The method further comprises the step of attaching the first connector component to a first article of manufacture, such as to a chair, a door panel, a picture frame, a flange, a cable, etc., at step 222. At step 224, the method comprises forming a second connector component, such as a pin, comprising the other one of the groove and the primary groove spaced from the secondary groove. At step 226, the method comprises attaching the second connector component to a second article of manufacture. By attaching at steps 222 and 226, the connector components are understood to include being capable of integration or singularly formed with the associated article of manufacture in addition to being capable of attaching in the normal sense, such as through mechanical means, welding, and bonding. Finally, at step 228, a restriction feature is attached or positioned in the first connector component that requires an appropriate insertion force to overcome or to have permission or authority to trigger an alarm. Note that while the disclosed sequence is provided with specificity, it can be done in a different order than described.

Figure 13:
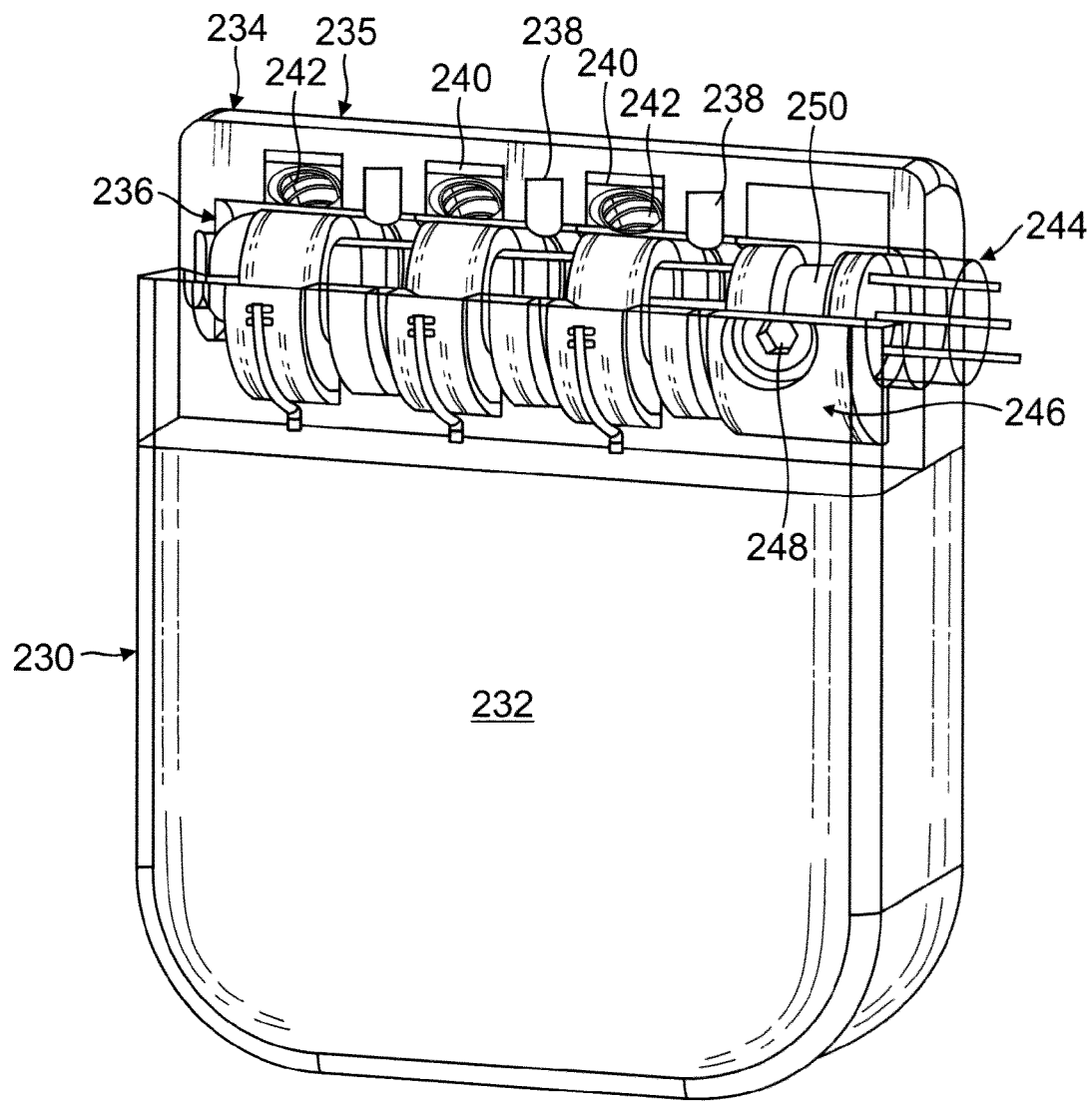
FIG. 13 is a partial cut-away perspective view of an implantable medical device (IMD) comprising a sealed housing and an in-line connector located in a header.

FIG. 13 is a perspective view of an implantable medical device (IMD) 230 provided in accordance with aspects of the present device, system, and method, which can include implantable cardio defibrillators, pacemakers, and programmable neurostimulator pulse generators. The IMD 230 comprises a sealed housing 232, which is known in the industry as a can or canned housing, and a header 234 comprising an in-line connector 236. The in-line connector 236 comprises a plurality of alternating seal elements 238 and conductive elements 240, of which only three alternating sets are shown with different numbers contemplated. Canted coil springs 242 are also incorporated, one in contact with each of the conductive elements 240. The header housing 235, the springs 242, the conductive elements 240, and the seal elements 238 have a common bore for receiving a lead cable 244. The lead cable 244 has terminal ends (not shown) that are positioned near an area of the body to be treated, such as near the heart for a cardiac heart pacemaker application. The cable 244 is configured to carry signals away from the canned housing 232 or vice versa for a therapeutic monitoring application. Additional information regarding IMDs and in-line connectors are disclosed in US Publication numbers 2008/0246231 and 2008/0255631, which are expressly incorporated herein by reference. Other IMDs and in-line connectors are also disclosed in co-pending application Ser. No. 12/717,732, filed Mar. 4, 2010, and Ser. No. 12/618,493, filed Nov. 13, 2009, the contents of each of which are expressly incorporated herein by reference.

To secure the lead cable 244 within the bore of the header, a retention block 246 is used, which comprises a set screw 248 for fastening against a corresponding surface 250 on the lead cable. The retention block 246 may be located at the inlet of the header housing 235, as shown, or at the far end of the header. In accordance with an aspect of the present device, system, and method, any of the connectors of FIGS. 1A, 2A, 3, 4, 5A, 6A and 7 may be used in place of the combination retention block 246 and groove 250 on the lead cable 244 of the header of the IMD 230. For example, any of the first connector components of FIGS. 1A, 2A, 3, 4, 5A, 6A and 7 may be used in place of the retention block 246 of FIG. 13 and instead of a single pin groove 250, a primary groove and a secondary groove are used with the lead cable 244 to permit a first latched position and a second latched position. Furthermore, the connector may be placed near the inlet as shown in FIG. 13 or at the far end of the header 234. Still furthermore, the modified retention mechanism using one of the connectors described in FIGS. 1A, 2A, 3, 4, 5A. 6A and 7 may incorporate a single pin groove on the lead cable 244 and two housing grooves for the retention block 246. Still furthermore, the connectors of FIGS. 1A, 2A, 3, 4, 5A, 6A and 7 may be used with any of the headers described in the '231 publication, the '631 publication, and the '732 application. If incorporated with the IMD, the first connector component is understood to include a through bore if incorporated at the entrance of the header and may include a through bore if incorporated at the far end of the header.

Figure 14:
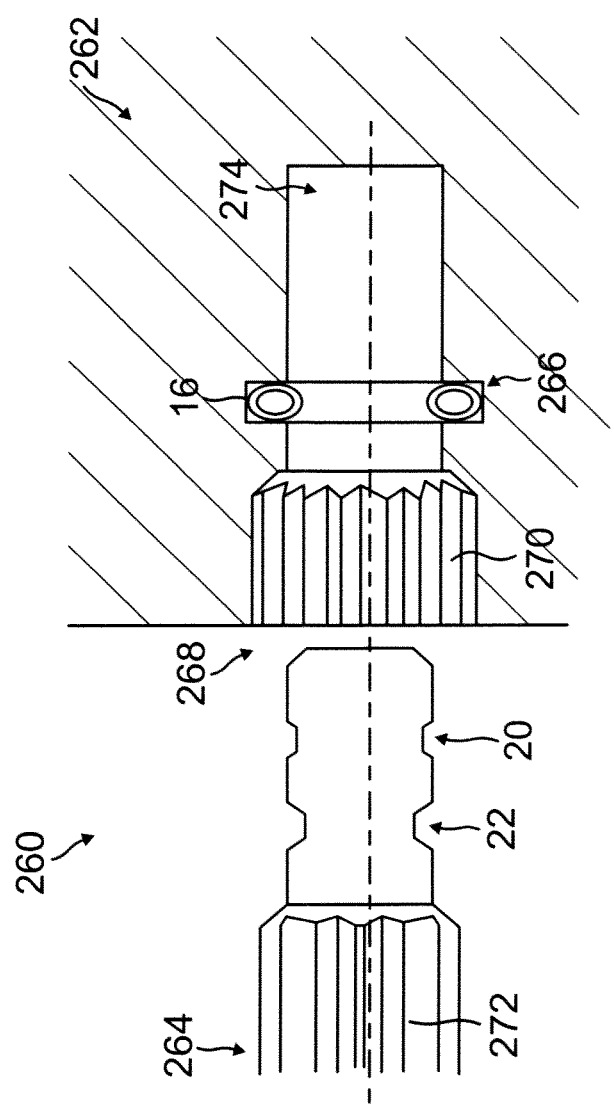
FIG. 14 is a schematic cross-sectional side view of an alternative dual direction connector, which shows a second connector component just before insertion into the bore of the first connector component.

FIG. 14 is a cross-sectional side view of yet another connector assembly 260 provided in accordance with aspects of the present device, system, and method. The connector assembly has a first connector component 262 with a first connector groove 266 and a second connector component 264 with a primary groove 20 and a secondary groove 22, similar to other connector assemblies discussed elsewhere herein. In the present embodiment, a restriction feature 268 in the form of fluted surfaces is incorporated. Fluted surfaces are similar to gear surfaces. In particular, the first connector component 262 incorporates a fluted surface 270, such as a fluted bore, for receiving a corresponding fluted surface 272, such as a fluted pin or shaft, on the second connector component 264. The second connector component 262 is rotated until the fluted surfaces are aligned, when then allows the second connector component to be further inserted into the bore to move to the second latched position to allow the spring 16 to rotate. The second connector component can then be removed.

Figure 15A:
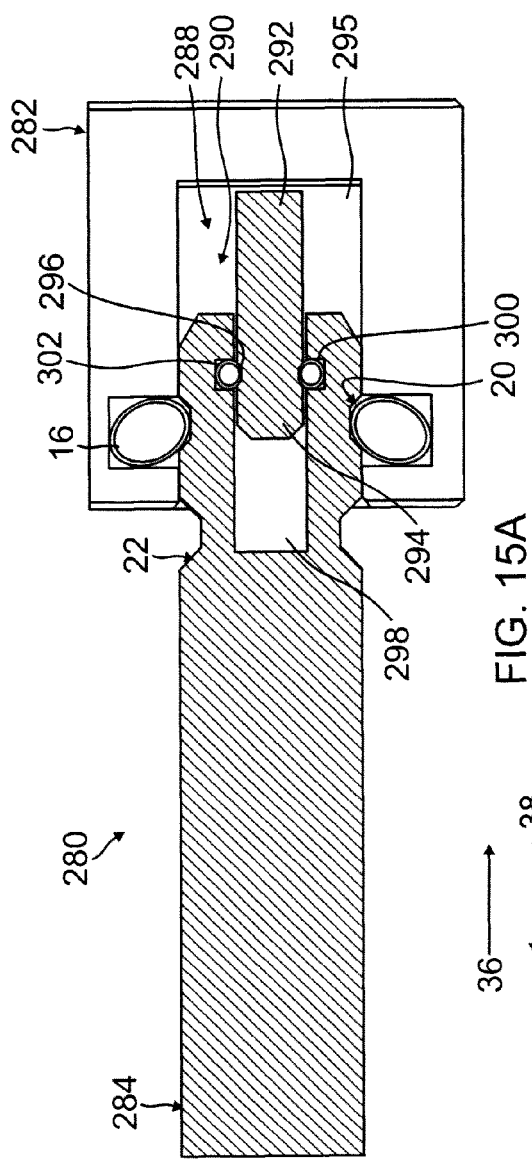
FIG. 15A shows a schematic cross-sectional side view of an alternative dual direction connector, which shows a second connector component located in a bore of a first connector component and a restriction feature restricting further advancement, which embodies an inner sub-connector assembly.

FIG. 15A is a cross-sectional side view of yet another connector assembly provided in accordance with aspects of the present device, system, and method, which is generally designated 280. Like the other connector assemblies and devices discussed elsewhere herein, the present connector assembly 280 has two latched positions and wherein a restriction feature is provided to restrict movement between the first latched position and the second latched position. As shown, the connector assembly 280 comprises a first connector component 282 and a second connector component 284, which are engaged to one another in the first latched positioned (FIG. 15A) by moving the second connector component 284 in the first direction 36 into the bore 295 of the first connector component. In the first latched position, the spring 16 is loaded along its major axis by the first connector groove 286 and the primary groove 20, which prevents the second connector component 284 from retracting in the second direction 38. As shown, the first connector component 282 is a housing and the second connector component 284 is a pin. In other embodiments, the name designation for the two is reversed.

In the present embodiment, a restriction feature 288 comprising a sub-connector assembly 290 comprising an inner pin 292 having a tapered nose section 294 and a groove 296, also referred as an inner pin groove, is provided. The inner pin 292 is sized and shaped to move into an inner bore 298 of the second connector body 284 to connect with an inner bore groove 300 and an inner spring 302 when the first connector and second connector components move to the first latched position. The inner spring 302 is preferably a radial canted coil spring. In an embodiment, the connection in the sub-connector assembly 290 permits unlatching in that the inner pin 292 can separate from the inner bore 298 after the two latch but for the restriction of the first latched position between the first connector component 282 and the second connector component 284, which prevents the second connector component 284 from moving in the second direction 38 until the spring 16 is rotated, as previously described. The length of the inner pin 292, the location of the inner pin groove 296, the depth of the inner bore 298, and the location of the inner groove 300 are selected so that the sub-connector 290 latches at about the same time or substantially simultaneously with the first latched position between the first and second connector components 282, 284.

Figure 15B:
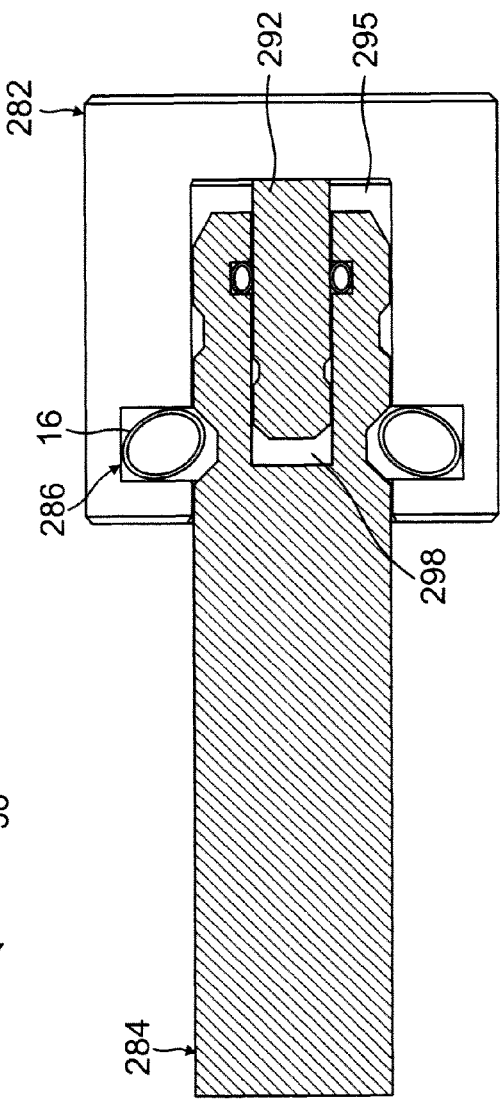
FIG. 15B shows a schematic cross-sectional side view of the dual direction connector of FIG. 15A with the first connector component engaged to the second connector component in a second latched position after overcoming the restriction force generated by the restriction feature.

FIG. 15B is a cross-sectional side view of the connector of FIG. 15A in a second latched position. As shown, the second connector component 284 is advanced further into the inner bore 298 of the first connector component 282 to unlatch the sub-connector 290 and move the outer or primary spring 16 to the combination first connector groove 286 and the relatively larger secondary groove 22. In moving the connector assembly 280 to the second latched position from the first latched position, it is understood that a force is required to unlatch the second connector component 284 from the first connector component 282 and an additional force is required to unlatch the inner pin 292 from the inner spring 302 and the inner bore groove 300. This additional force provides a restriction feature that must be overcome before the connector 280 assembly can be moved to the second latched position.

In the second latched position, the spring 16 is allowed to rotate due to the relatively larger secondary groove 22. The second connector component 284 can now be removed from the first connector component 282 by moving in the second direction 38. During this movement in the second direction 38, the outer spring 16, when viewing only the upper part of the spring in FIG. 15B, rotates clockwise and compresses along the minor axis, i.e., the short axis. As the second connector component 284 moves in the second direction 38 to separate from the first connector component, the outer spring 16 latches again with the primary groove 20 and the inner spring 302 latches again with the inner pin groove 296. However, because the outer spring 16 has rotated and the inner spring 292 is not loaded along its major axis, complete separation of the second connector component from the first connector component is permitted. In practice, the connector 280 may be used with first and second articles of manufacture to secure the two articles together, similar to other connectors discussed elsewhere herein.

Thus, the present connector assembly may be understood to include a first connector component and a second connector component having a first latched position and a second latched position and wherein the connector is restricted from moving from the first latched position to the second latched position by a restriction feature. The connector assembly is further understood to permit latching in the second latched position only after overcoming the restriction feature. In one embodiment, the restriction feature is overcome by applying an insertion force that not only separates the first connector component from the second connector component, but also a force that overcomes a latching force of a sub-connector assembly. Thus, broadly speaking, the connector assembly comprises multi-latch points with at least one restriction feature between the multi-latch points. In a specific embodiment, the restriction feature is a sub-assembly connector comprising an inner pin projecting into an inner bore of the secondary component.

The connector may be used by inserting the second connector component 284 into the bore 298 of the first connector component 282 until the spring 16 is in a first latched position FIG. 15A. However, the spring 16 cannot move to a second latched position. FIG. 15B, until a restriction feature 288 is overcome, which requires an additional insertion force to overcome the latching of a sub-connector assembly. At this time, the second connector component 284 can move to the second latched position (FIG. 15B) to allow the outer spring 16 to rotate to then separate from the first connector component.

Although limited embodiments of dual directional latch connectors and assemblies and their components have been specifically described and illustrated herein, many modifications and variations will be apparent to those skilled in the art. For example, the various connector components may be used with other articles of manufacture not specifically discussed herein but are understood to be usable therewith as means for removably attaching one article to another article during the course of fabricating, manufacturing, or assembling the articles. Furthermore, it is understood and contemplated that features specifically discussed for one connector or assembly may be adopted for inclusion with another connector or assembly provided the functions are compatible. For example, while the various first connector components are discussed with a single groove and the various second connector components are discussed with a primary groove and a secondary groove, the reverse arrangement is possible wherein the first connector components have the primary and secondary grooves while the second connector component has a single groove. Still furthermore, wherein the disclosure describes moving a component in a first direction or a second direction, it is possible to hold one a different component steady while moving another component or moving both components at the same time but relative to one another. Accordingly, it is to be understood that the connector assemblies and their components constructed according to principles of the disclosed device, system, and method may be embodied other than as specifically described herein. The disclosure is also defined in the following claims.

What is claimed is:

1. A connector comprising a first connector component mated with a second connector component, a groove located in or on the first connector component or the second connector component and a pair of grooves located in or on the other one of the first connector component or the second connector component;
   the groove having two sidewalls and a bottom wall;
   the pair of grooves comprises a first groove having a first depth and a second groove having a second depth, which has a larger value than the first depth;
   an axial canted coil spring comprising a plurality of coils positioned in the first groove and the groove and is movable to be seated in the second groove and the groove; each of said plurality of coils having a major axis and a minor axis and being loaded along the major axis by the first groove and the groove; and
   wherein a restriction feature prevents the first connector component from moving relative to the second connector component until overcome by an insertion force to restrict the canted coil spring from being engaged by the second groove and the groove; said restriction feature being selected from the group consisting of magnets creating opposed magnetic forces, electromagnetic forces, a fluid pressure relief bore and a seal, a spring, a shear pin, a collapsible structure, a deflectable structure, a switch trigger, a normally open contact switch, a conductive section, a conductive insert, fluted surfaces, and an inner pin having a groove with a spring.

2. The connector of claim 1, wherein the first connector component is a pin or a housing and the second connector component is the other one of the pin or the housing.

3. The connector of claim 2, wherein the housing has a bore and the bore has a constant inside diameter.

4. The connector of claim 3, wherein the housing has an end wall covering one end of the bore.

5. The connector of claim 1, wherein the second connector component is attached to an article of manufacture.

6. The connector of claim 1, further comprising an implantable medical device and wherein the first connector component is located in a header of the implantable medical device.

7. The connector of claim 1, further comprising an article of manufacture attached to the first connector component or the second connector component.

8. A connector comprising:
   a housing comprising a bore and a housing groove having a housing groove depth;
   a pin comprising a pin groove having a pin groove depth;
   a second groove located adjacent the housing groove or the pin groove, the second groove having a second groove depth that differs from the housing groove depth and the pin groove depth;
   an axial canted coil spring comprising a plurality of coils disposed in the bore in a first spring position in a first common groove defined by a combination of the housing groove and the pin groove and is movable relative to the pin and the housing to a second common groove defined by a combination of the housing groove and the second groove or a combination of the pin groove and the second groove; each of said plurality of coils having a major axis and a minor axis and being loaded along the major axis by the housing groove and the pin groove; and
   wherein a restriction feature is provided to restrict relative movement between the housing and the pin to restrict the axial canted coil spring from moving to the second common groove until overcome by an insertion force; said restriction feature being selected from the group consisting of magnets creating opposed magnetic forces, electromagnetic forces, a fluid pressure relief bore and a seal, a spring, a shear pin, a collapsible structure, a deflectable structure, a switch trigger, a normally open contact switch, a conductive section, a conductive insert, fluted surfaces, sub-connector assembly, and an inner pin having a groove with a spring.

9. The connector of claim 8, further comprising an article of manufacture attached to the pin or the housing.

10. The connector of claim 8, further comprising an implantable medical device and wherein the first housing is located in a header of the implantable medical device.

11. The connector of claim 8, wherein the second groove comprises a ring and a conductive section disposed therein for electrical communication with the axial canted coil spring.

12. The connector of claim 8, further comprising an electrical wire connected to the first connector component, the second connector component, or both.

13. The connector of claim 8, wherein the sub-connector assembly comprises a sub-connector pin having an external groove latched to a sub-connector bore comprising an inner groove and a canted coil spring.

14. The connector of claim 8, wherein the housing has a bore and the bore has a constant inside diameter.

15. The connector of claim 14, wherein the housing has an end wall covering one end of the bore.

* * * * *